US009757512B2

(12) United States Patent
Mernoe et al.

(10) Patent No.: US 9,757,512 B2
(45) Date of Patent: Sep. 12, 2017

(54) WEARABLE INSULIN DISPENSING DEVICE, AND A COMBINATION OF SUCH A DEVICE AND A PROGRAMMING CONTROLLER

(71) Applicant: Bigfoot Biomedical, Inc., Milpitas, CA (US)

(72) Inventors: Morten Mernoe, Copenhagen (DK); Michael Gorm Lyngsie, Gentofte (DK)

(73) Assignee: Bigfoot Biomedical, Inc., Milpitas, CA (US)

( * ) Notice: Subject to any disclaimer, the term of this patent is extended or adjusted under 35 U.S.C. 154(b) by 0 days.

(21) Appl. No.: 15/062,401

(22) Filed: Mar. 7, 2016

(65) Prior Publication Data

US 2016/0184513 A1   Jun. 30, 2016

Related U.S. Application Data

(63) Continuation of application No. 14/449,439, filed on Aug. 1, 2014, now Pat. No. 9,308,319, which is a
(Continued)

(30) Foreign Application Priority Data

Nov. 5, 2002 (DK) .................................. 200201702
Dec. 23, 2002 (DK) .................................. 200202006

(51) Int. Cl.
*A61M 5/142* (2006.01)
*A61M 5/172* (2006.01)
(Continued)

(52) U.S. Cl.
CPC ...... *A61M 5/14248* (2013.01); *A61M 5/1452* (2013.01); *A61M 5/14566* (2013.01);
(Continued)

(58) Field of Classification Search
CPC .............. A61M 5/14248; A61M 5/158; A61M 5/1452; A61M 5/14566; A61M 5/172; A61M 2202/04; A61M 2205/0238; A61M 5/14546; A61M 2205/0266; A61M 2205/3592; A61M 2205/581;
(Continued)

(56) References Cited

U.S. PATENT DOCUMENTS 2,605,765 A    8/1952   Kollsman
3,886,938 A    6/1975   Szabo et al.
(Continued)

FOREIGN PATENT DOCUMENTS

CA       2543545       5/2005
DE    196 27 619 A    1/1998
(Continued)

OTHER PUBLICATIONS

Accu-Chek Spirit, "Pump Therapy Made for You," Roche, 2006, 6 pages.
(Continued)

*Primary Examiner* — Manuel Mendez
(74) *Attorney, Agent, or Firm* — Fish & Richardson P.C.

(57) ABSTRACT

A disposable, wearable, self-contained insulin dispensing device includes a housing and an insulin source in the housing that is connected to a catheter for injecting insulin into a user.

20 Claims, 19 Drawing Sheets

Related U.S. Application Data continuation of application No. 13/705,638, filed on Dec. 5, 2012, now Pat. No. 8,801,655, which is a continuation of application No. 12/818,830, filed on Jun. 18, 2010, now Pat. No. 8,469,920, which is a continuation of application No. 11/157,479, filed on Jun. 21, 2005, now Pat. No. 7,785,288, which is a continuation of application No. PCT/DK03/00916, filed on Dec. 19, 2003, and a continuation-in-part of application No. 11/121,708, filed on May 4, 2005, now Pat. No. 7,887,511, which is a continuation of application No. PCT/DK03/00753, filed on Nov. 4, 2003.

(51) Int. Cl.
  *A61M 5/145* (2006.01)
  *A61M 5/158* (2006.01)
  *A61M 5/31* (2006.01)
  *A61M 5/315* (2006.01)

(52) U.S. Cl.
  CPC .......... *A61M 5/158* (2013.01); *A61M 5/172* (2013.01); *A61M 5/14546* (2013.01); *A61M 2005/14268* (2013.01); *A61M 2005/1581* (2013.01); *A61M 2005/3109* (2013.01); *A61M 2005/31518* (2013.01); *A61M 2202/04* (2013.01); *A61M 2205/0238* (2013.01); *A61M 2205/0266* (2013.01); *A61M 2205/3592* (2013.01); *A61M 2205/581* (2013.01)

(58) Field of Classification Search
  CPC ........... A61M 2205/14268; A61M 2005/1581; A61M 2005/3109
  USPC .............. 604/65–67, 151, 131; 128/DIG. 12, 128/DIG. 13
  See application file for complete search history.

(56) References Cited

U.S. PATENT DOCUMENTS

| | | | |
|---|---|---|---|
| 4,077,405 A | 3/1978 | Haerten et al. | |
| 4,231,368 A | 11/1980 | Becker | |
| 4,265,241 A | 5/1981 | Portner et al. | |
| 4,300,554 A | 11/1981 | Hessberg et al. | |
| 4,313,439 A | 2/1982 | Babb et al. | |
| 4,398,908 A | 8/1983 | Siposs | |
| 4,435,173 A | 3/1984 | Siposs et al. | |
| 4,443,218 A | 4/1984 | DeCant, Jr. et al. | |
| 4,493,704 A | 1/1985 | Beard et al. | |
| 4,529,401 A | 7/1985 | Leslie et al. | |
| 4,583,976 A | 4/1986 | Ferguson | |
| 4,850,817 A | 7/1989 | Nason et al. | |
| 5,045,064 A | 9/1991 | Idriss | |
| 5,088,981 A | 2/1992 | Howson et al. | |
| 5,176,632 A | 1/1993 | Bernardi | |
| 5,190,522 A | 3/1993 | Wojcicki et al. | |
| 5,250,027 A | 10/1993 | Lewis et al. | |
| 5,261,882 A | 11/1993 | Sealfon | |
| 5,314,412 A | 5/1994 | Rex | |
| 5,335,994 A | 8/1994 | Weynant Nee Girones | |
| 5,338,157 A | 8/1994 | Blomquist | |
| 5,342,180 A | 8/1994 | Daoud | |
| 5,395,340 A | 3/1995 | Lee | |
| 5,411,487 A | 5/1995 | Castagna | |
| 5,545,143 A | 8/1996 | Fischell | |
| 5,551,850 A | 9/1996 | Williamson et al. | |
| 5,569,186 A | 10/1996 | Lord et al. | |
| 5,626,566 A | 5/1997 | Petersen et al. | |
| 5,637,095 A | 6/1997 | Nason et al. | |
| 5,665,065 A | 9/1997 | Colman et al. | |
| 5,741,216 A | 4/1998 | Hemmingsen et al. | |
| 5,772,635 A | 6/1998 | Dastur et al. | |
| 5,800,420 A | 9/1998 | Gross et al. | |
| 5,816,306 A | 10/1998 | Giacomel | |
| 5,852,803 A | 12/1998 | Ashby, III | |
| 5,919,167 A | 7/1999 | Mulhauser et al. | |
| 5,925,018 A | 7/1999 | Ungerstedt | |
| 5,928,201 A | 7/1999 | Poulsen et al. | |
| 5,947,934 A | 9/1999 | Hansen et al. | |
| 5,951,530 A | 9/1999 | Steengaard et al. | |
| 5,957,889 A | 9/1999 | Poulsen et al. | |
| 5,984,894 A | 11/1999 | Poulsen et al. | |
| 5,984,897 A | 11/1999 | Petersen et al. | |
| 5,997,475 A | 12/1999 | Bortz | |
| 6,003,736 A | 12/1999 | Ljunggren | |
| 6,010,485 A | 1/2000 | Buch-Rasmussen et al. | |
| 6,033,377 A | 3/2000 | Rasmussen et al. | |
| 6,045,537 A | 4/2000 | Klitmose | |
| 6,074,372 A | 6/2000 | Hansen | |
| 6,110,149 A | 8/2000 | Klitgaard et al. | |
| 6,156,014 A | 12/2000 | Petersen et al. | |
| 6,171,276 B1 | 1/2001 | Lippe et al. | |
| 6,231,540 B1 | 5/2001 | Smedegaard | |
| 6,248,067 B1 | 6/2001 | Causey, III et al. | |
| 6,248,090 B1 | 6/2001 | Jensen et al. | |
| 6,248,093 B1 | 6/2001 | Moberg | |
| 6,270,455 B1 * | 8/2001 | Brown ................. | A61B 5/0022 128/920 |
| 6,277,098 B1 | 8/2001 | Klitmose et al. | |
| 6,302,855 B1 | 10/2001 | Lav et al. | |
| 6,302,869 B1 | 10/2001 | Klitgaard | |
| 6,375,638 B2 | 4/2002 | Nason et al. | |
| 6,379,339 B1 | 4/2002 | Klitgaard et al. | |
| 6,381,496 B1 | 4/2002 | Meadows et al. | |
| 6,404,098 B1 | 6/2002 | Kayama et al. | |
| 6,427,088 B1 | 7/2002 | Bowman, IV et al. | |
| 6,461,331 B1 | 10/2002 | Van Antwerp | |
| 6,474,219 B2 | 11/2002 | Klitmose et al. | |
| 6,485,461 B1 | 11/2002 | Mason et al. | |
| 6,508,788 B2 | 1/2003 | Preuthun | |
| 6,524,280 B2 | 2/2003 | Hansen et al. | |
| 6,533,183 B2 | 3/2003 | Aasmul et al. | |
| 6,537,251 B2 | 3/2003 | Klitmose | |
| 6,540,672 B1 | 4/2003 | Simonsen et al. | |
| 6,544,229 B1 | 4/2003 | Danby et al. | |
| 6,547,764 B2 | 4/2003 | Larsen et al. | |
| 6,551,276 B1 | 4/2003 | Mann et al. | |
| 6,554,798 B1 | 4/2003 | Mann et al. | |
| 6,554,800 B1 | 4/2003 | Nezhadian et al. | |
| 6,558,320 B1 | 5/2003 | Causey, III et al. | |
| 6,558,351 B1 | 5/2003 | Steil et al. | |
| 6,562,001 B2 | 5/2003 | Lebel et al. | |
| 6,562,011 B1 | 5/2003 | Buch-Rasmussen et al. | |
| 6,564,105 B2 | 5/2003 | Starkweather et al. | |
| 6,569,126 B1 | 5/2003 | Poulsen et al. | |
| 6,571,128 B2 | 5/2003 | Lebel et al. | |
| 6,577,899 B2 | 6/2003 | Lebel et al. | |
| 6,582,404 B1 | 6/2003 | Klitgaard et al. | |
| 6,585,644 B2 | 7/2003 | Lebel et al. | |
| 6,585,699 B2 | 7/2003 | Ljunggreen et al. | |
| 6,605,067 B1 | 8/2003 | Larsen | |
| 6,613,019 B2 | 9/2003 | Munk | |
| 6,641,533 B2 | 11/2003 | Causey, III et al. | |
| 6,648,821 B2 | 11/2003 | Lebel et al. | |
| 6,650,951 B1 | 11/2003 | Jones et al. | |
| 6,656,158 B2 | 12/2003 | Mahoney et al. | |
| 6,656,159 B2 | 12/2003 | Flaherty | |
| 6,659,948 B2 | 12/2003 | Lebel et al. | |
| 6,659,978 B1 | 12/2003 | Kasuga et al. | |
| 6,659,980 B2 | 12/2003 | Moberg et al. | |
| 6,663,602 B2 | 12/2003 | Møller | |
| 6,668,196 B1 | 12/2003 | Villegas et al. | |
| 6,669,669 B2 | 12/2003 | Flaherty et al. | |
| 6,687,546 B2 | 2/2004 | Lebel et al. | |
| 6,691,043 B2 | 2/2004 | Ribeiro, Jr. | |
| 6,692,457 B2 | 2/2004 | Flaherty | |
| 6,692,472 B2 | 2/2004 | Hansen et al. | |
| 6,694,191 B2 | 2/2004 | Starkweather et al. | |
| 6,699,218 B2 | 3/2004 | Flaherty et al. | |
| 6,702,779 B2 | 3/2004 | Connelly et al. | |
| 6,715,516 B2 | 4/2004 | Ohms et al. | |

(56) References Cited

U.S. PATENT DOCUMENTS

| | | | |
|---|---|---|---|
| 6,716,198 B2 | 4/2004 | Larsen | |
| 6,723,072 B2 | 4/2004 | Flaherty et al. | |
| 6,733,446 B2 | 5/2004 | Lebel et al. | |
| 6,736,796 B2 | 5/2004 | Shekalim | |
| 6,740,059 B2 | 5/2004 | Flaherty | |
| 6,740,072 B2 | 5/2004 | Starkweather et al. | |
| 6,740,075 B2 | 5/2004 | Lebel et al. | |
| 6,744,350 B2 | 6/2004 | Blomquist | |
| 6,749,587 B2 | 6/2004 | Flaherty | |
| 6,752,787 B1 | 6/2004 | Causey, III et al. | |
| 6,758,810 B2 | 7/2004 | Lebel et al. | |
| 6,768,425 B2 | 7/2004 | Flaherty et al. | |
| 6,780,156 B2 | 8/2004 | Haueter et al. | |
| 6,786,246 B2 | 9/2004 | Ohms et al. | |
| 6,786,890 B2 | 9/2004 | Preuthun et al. | |
| 6,796,970 B1 | 9/2004 | Klitmose et al. | |
| 6,799,149 B2 | 9/2004 | Hartlaub | |
| 6,809,653 B1 | 10/2004 | Mann et al. | |
| 6,810,290 B2 | 10/2004 | Lebel et al. | |
| 6,811,533 B2 | 11/2004 | Lebel et al. | |
| 6,811,534 B2 | 11/2004 | Bowman, IV et al. | |
| 6,813,519 B2 | 11/2004 | Lebel et al. | |
| 6,827,702 B2 | 12/2004 | Lebel et al. | |
| 6,830,558 B2 | 12/2004 | Flaherty et al. | |
| 6,852,104 B2 | 2/2005 | Blomquist | |
| 6,854,620 B2 | 2/2005 | Ramey | |
| 6,854,653 B2 | 2/2005 | Eilersen | |
| 6,855,129 B2 | 2/2005 | Jensen et al. | |
| 6,872,200 B2 | 3/2005 | Mann et al. | |
| 6,873,268 B2 | 3/2005 | Lebel et al. | |
| 6,878,132 B2 | 4/2005 | Kipfer | |
| 6,893,415 B2 | 5/2005 | Madsen et al. | |
| 6,899,695 B2 | 5/2005 | Herrera | |
| 6,899,699 B2 | 5/2005 | Enggaard | |
| 6,922,590 B1 | 7/2005 | Whitehurst | |
| 6,936,006 B2 | 8/2005 | Sabra | |
| 6,936,029 B2 | 8/2005 | Mann et al. | |
| 6,945,961 B2 | 9/2005 | Miller et al. | |
| 6,948,918 B2 | 9/2005 | Hansen | |
| 6,950,708 B2 | 9/2005 | Bowman, IV et al. | |
| 6,960,192 B1 | 11/2005 | Flaherty et al. | |
| 6,979,326 B2 | 12/2005 | Mann et al. | |
| 6,997,911 B2 | 2/2006 | Klitmose | |
| 6,997,920 B2 | 2/2006 | Mann et al. | |
| 7,005,078 B2 | 2/2006 | Van Lintel et al. | |
| 7,008,399 B2 | 3/2006 | Larson et al. | |
| 7,014,625 B2 | 3/2006 | Bengtsson | |
| 7,018,360 B2 | 3/2006 | Flaherty et al. | |
| 7,025,743 B2 | 4/2006 | Mann | |
| 7,029,455 B2 | 4/2006 | Flaherty | |
| 7,054,836 B2 | 5/2006 | Christensen et al. | |
| 7,104,972 B2 | 9/2006 | Møller et al. | |
| 7,128,727 B2 | 10/2006 | Flaherty et al. | |
| 7,133,329 B2 | 11/2006 | Skyggebjerg et al. | |
| 7,232,423 B2 | 6/2007 | Mernoe | |
| 7,785,288 B2 | 8/2010 | Mernoe | |
| 8,469,920 B2 | 6/2013 | Mernoe et al. | |
| 2001/0056262 A1 | 12/2001 | Cabiri | |
| 2002/0004651 A1 | 1/2002 | Ljndggreen et al. | |
| 2002/0007154 A1 | 1/2002 | Hansen et al. | |
| 2002/0040208 A1 | 4/2002 | Flaherty et al. | |
| 2002/0091358 A1 | 7/2002 | Klitmose | |
| 2002/0126036 A1 | 9/2002 | Flaherty et al. | |
| 2003/0055380 A1 | 3/2003 | Flaherty | |
| 2003/0065308 A1 | 4/2003 | Lebel et al. | |
| 2003/0088238 A1 | 5/2003 | Poulsen | |
| 2003/0199825 A1 | 10/2003 | Flaherty | |
| 2003/0216683 A1 | 11/2003 | Shekalim | |
| 2004/0010207 A1 | 1/2004 | Flaherty et al. | |
| 2004/0019325 A1 | 1/2004 | Shekalim | |
| 2004/0064088 A1 | 4/2004 | Gorman et al. | |
| 2004/0064096 A1 | 4/2004 | Flaherty et al. | |
| 2004/0078028 A1 | 4/2004 | Flaherty et al. | |
| 2004/0087894 A1 | 5/2004 | Flaherty | |
| 2004/0092865 A1 | 5/2004 | Flaherty et al. | |
| 2004/0092878 A1 | 5/2004 | Flaherty | |
| 2004/0116866 A1 | 6/2004 | Gorman et al. | |
| 2004/0127844 A1 | 7/2004 | Flaherty | |
| 2004/0153032 A1 | 8/2004 | Garribotto et al. | |
| 2004/0171983 A1 | 9/2004 | Sparks et al. | |
| 2004/0176727 A1 | 9/2004 | Shekalim | |
| 2004/0204673 A1 | 10/2004 | Flaherty | |
| 2004/0220551 A1 | 11/2004 | Flaherty et al. | |
| 2004/0235446 A1 | 11/2004 | Flaherty et al. | |
| 2004/0260233 A1 | 12/2004 | Garibotto et al. | |
| 2005/0021005 A1 | 1/2005 | Flaherty et al. | |
| 2005/0022274 A1 | 1/2005 | Campbell et al. | |
| 2005/0065760 A1 | 3/2005 | Murtfeldt et al. | |
| 2005/0090808 A1 | 4/2005 | Malave et al. | |
| 2005/0095063 A1 | 5/2005 | Fathallah | |
| 2005/0160858 A1 | 7/2005 | Mernoe | |
| 2005/0171512 A1 | 8/2005 | Flaherty | |
| 2005/0182366 A1 | 8/2005 | Vogt et al. | |
| 2005/0192561 A1 | 9/2005 | Mernoe | |
| 2005/0203461 A1 | 9/2005 | Flaherty et al. | |
| 2005/0215982 A1 | 9/2005 | Malave et al. | |
| 2005/0222645 A1 | 10/2005 | Malave et al. | |
| 2005/0238507 A1 | 10/2005 | DiIanni et al. | |
| 2005/0245878 A1 | 11/2005 | Mernoe et al. | |
| 2005/0251097 A1 | 11/2005 | Mernoe | |
| 2005/0267402 A1 | 12/2005 | Stewart et al. | |
| 2005/0273059 A1 | 12/2005 | Mernoe et al. | |
| 2006/0041229 A1 | 2/2006 | Garibotto et al. | |
| 2006/0069382 A1 | 3/2006 | Pedersen | |
| 2006/0074381 A1 | 4/2006 | Malave et al. | |
| 2006/0095014 A1 | 5/2006 | Ethelfeld | |
| 2006/0135913 A1 | 6/2006 | Ethelfeld | |
| 2006/0142698 A1 | 6/2006 | Ethelfeld | |
| 2006/0178633 A1 | 8/2006 | Garibotto et al. | |
| 2006/0184119 A1 | 8/2006 | Remde et al. | |
| 2006/0200073 A1 | 9/2006 | Radmer et al. | |
| 2006/0206054 A1 | 9/2006 | Shekalim | |
| 2006/0247581 A1 | 11/2006 | Pedersen et al. | |
| 2007/0073228 A1 | 3/2007 | Mernoe et al. | |
| 2007/0073236 A1 | 3/2007 | Mernoe et al. | |
| 2007/0124002 A1 | 5/2007 | Estes et al. | |
| 2007/0156092 A1 | 7/2007 | Estes et al. | |
| 2007/0167905 A1 | 7/2007 | Estes et al. | |
| 2007/0167912 A1 | 7/2007 | Causey et al. | |
| 2013/0102964 A1 | 4/2013 | Mernoe | |

FOREIGN PATENT DOCUMENTS

| | | |
|---|---|---|
| DE | 102 36 669 | 2/2004 |
| EP | 0 496 141 | 7/1992 |
| EP | 0 612 004 | 8/1994 |
| EP | 0 580 723 | 10/1995 |
| EP | 1 045 146 | 10/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| FR | 2 585 252 | 1/1987 |
| GB | 747 701 | 4/1956 |
| GB | 2 218 831 | 11/1989 |
| JP | 2000-513974 | 10/2000 |
| JP | 2002-507459 | 3/2002 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/48546 | 9/1999 |
| WO | WO 01/91822 | 12/2001 |
| WO | WO 01/91833 | 12/2001 |
| WO | WO 02/10469 | 2/2002 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 2004/056412 | 7/2004 |
| WO | WO 2004/110526 | 12/2004 |

(56) References Cited

FOREIGN PATENT DOCUMENTS

| WO | WO 2005/002652 | 1/2005 |
| WO | WO 2005/039673 | 5/2005 |
| WO | WO 2005/039763 | 5/2005 |
| WO | WO 2005/072794 | 8/2005 |
| WO | WO 2005/072795 | 8/2005 |
| WO | WO 2006/105792 | 10/2006 |
| WO | WO 2006/105793 | 10/2006 |
| WO | WO 2006/105794 | 10/2006 |

OTHER PUBLICATIONS

Debiotech News Release, "Debiotech reveals its new miniaturized Disposable Insulin Nanopump™ for Diabetes therapy," available at http://www.debiotech.com/news/nw_159.html, Apr. 24, 2006, 3 pages.
Japanese Patent Office, Office Action JP 2004-561091, mailed Jul. 23, 2009 and English Translation, 7 pages.
Medtronic News Release, "Medtronic Receives FDA Approval for Worlds' First Insunlin Pump with Real-time Continuous Glucose Monitoring," Apr. 13, 2006, 3 pages.
OmniPod Insulin Management System—Investor Relations—Press Release, Feb. 1, 2005, http://investors.insulet.com/phoenix/zhtml?c=209336&p=irol-newsArticle&ID=988708&highlight=, 1 page.
OmniPod Quick Start Guide, 2007, 2 pages.
Patent Abstracts of Japan vol. 1999, No. 4, and JP 11 010036, Apr. 30, 1999 and Jan. 19, 1999, Toray Ind. Inc.
The Medtronic Diabetes Connections, 2006, 6 pages.
Xilas Temp Touch, "The latest in high-tech and convenient devices," DOCNews, vol. 2, No. 7, Jul. 1, 2005, http://docnews.diabetesjournals.ord/cgi/content/full/2/7/13, 3 pages.

\* cited by examiner

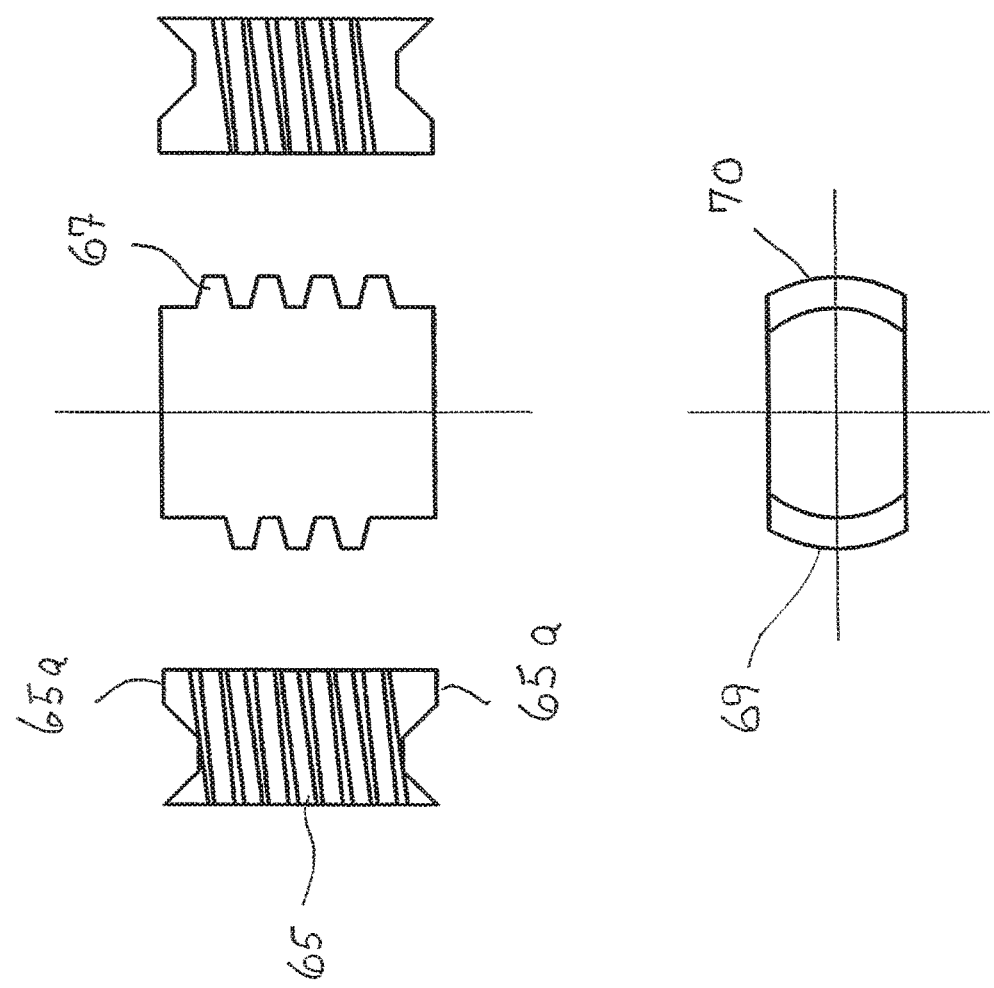

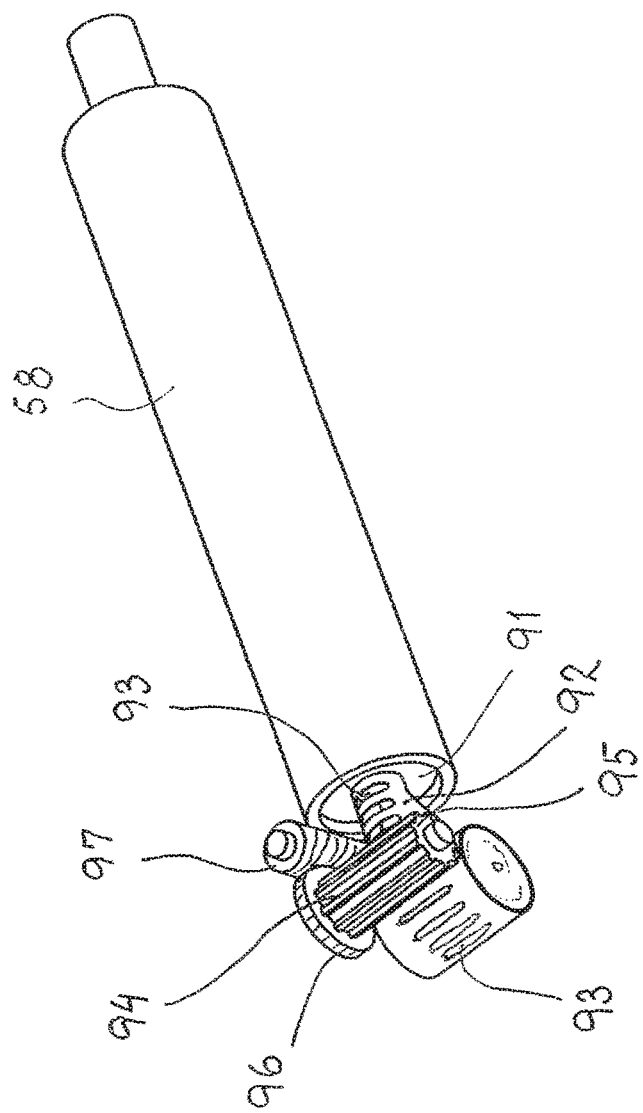

WEARABLE INSULIN DISPENSING DEVICE, AND A COMBINATION OF SUCH A DEVICE AND A PROGRAMMING CONTROLLER

CROSS-REFERENCE TO RELATED APPLICATIONS

This application is a continuation of U.S. patent application Ser. No. 14/449,439 (now U.S. Pat. No. 9,308,319) filed Aug. 1, 2014, which is a continuation of U.S. patent application Ser. No. 13/705,638 (now U.S. Pat. No. 8,801,655) filed Dec. 5, 2012, which is a continuation of U.S. patent application Ser. No. 12/818,830 (now U.S. Pat. No. 8,469,920) filed on Jun. 18, 2010, which is a continuation of U.S. patent application Ser. No. 11/157,479 (now U.S. Pat. No. 7,785,288) filed on Jun. 21, 2005, which is (i) a continuation of International Application No. PCT/DK2003/000916 (Pub. No. WO2004/056412), filed Dec. 19, 2003, which claims priority to Denmark Patent Application No. 200202006 filed on Dec. 23, 2002, and (ii) a continuation-in-part of U.S. application Ser. No. 11/121,708 (now U.S. Pat. No. 7,887,511), filed May 4, 2005, which is a Continuation of International Application No. PCT/DK2003/000753 (Pub. No. WO2004/041330), filed Nov. 4, 2003, which claims priority to Denmark Patent Application No. 200201702 filed on Nov. 5, 2002. The disclosures of all of the aforesaid related applications are incorporated herein by reference.

BACKGROUND

The present invention relates generally to wearable medicine dispensing devices, particularly insulin dispensing devices.

In connection with injection of insulin for treating Type I and Type II Diabetes extremely important features are simplicity of operation, reliability, cost and flexibility, which all are related to the issue of compliance which particularly in the cases of relatively mild Type II diabetes is a problem with important consequences regarding the success rate in treating the patients.

SUMMARY

The main object of the invention is to provide a wearable medicine, particularly insulin dispensing device having features and operation characteristics supporting and easing compliance by the users of the device.

The present invention provides a disposable, wearable, self-contained medicine, particularly insulin dispensing device comprising
  a housing,
  an insulin source in said housing,
  a pump means in said housing and adapted for pumping insulin from said insulin source to a catheter for injection of said insulin in a user of the device and, said catheter being associated with said housing and projecting generally perpendicularly to a generally planar surface of said housing intended for abutting a skin surface of a user of the device,
  an adhesive layer provided on said planar surface for adhering said planar surface to said skin surface, and
  a removable release sheet covering said adhesive layer for protecting said adhesive layer prior to use of said dispensing device, said release sheet being provided with catheter protection means to enclose and protect an end portion of said catheter such that removal of said release sheet for exposing said adhesive layer exposes said end portion.

Hereby, in a simple, reliable and cost-effective manner a device is provided which is easy to apply and still in an effective manner protects the catheter against damage and contamination until use of the device is initiated.

In another aspect, the invention provides a disposable, wearable, self-contained medicine, particularly insulin dispensing device comprising
  a housing,
  an insulin source in said housing,
  a pump means in said housing and adapted for pumping insulin from said insulin source to a catheter for injection of said insulin in a user of the device and, said catheter being associated with said housing and projecting generally perpendicularly to a generally planar surface of said housing intended for abutting a skin surface of a user of the device,
  an adhesive layer provided on said planar surface for adhering said planar surface to said skin surface,
  a combined microphone and loudspeaker associated with said housing, preferably arranged inside said housing, and
  recording and play back means connected to said combined microphone and loudspeaker and associated with said housing, preferably arranged inside said housing, such that verbal messages may be recorded and played back by said dispensing device.

Hereby a device promoting simple communication between a health care provider and the user is provided with readily understandable operation and with good effect on the compliance rate.

In yet another aspect, the invention provides a disposable, wearable, self-contained medicine, particularly insulin dispensing device comprising
  a housing,
  an insulin source in said housing,
  a pump means in said housing and adapted for pumping insulin from said insulin source to a catheter for injection of said insulin in a user of the device, and
  an actuator for said pump means, said actuator comprising a shape memory alloy wire, said actuator preferably further comprising a ratchet gear or pawl wheel, a pawl adapted for co-operating with said pawl wheel and connected to one end of said shape memory alloy wire and a spring means connected to said pawl, the connections between said pawl and said wire and said pawl and said spring means being such that contraction of said wire rotates said pawl wheel against the spring force of said spring means.

Hereby a pump means requiring very low energy and with a high degree of reliability is provided at a relatively low cost.

In a yet further aspect, the invention relates to a disposable, wearable, self-contained medicine, particularly insulin dispensing device comprising
  a housing,
  an insulin source in said housing,
  a pump means in said housing and adapted for pumping insulin from said insulin source to a catheter for injection of said insulin in a user of the device,
  an actuator for said pump means, preferably an actuator comprising a shape memory alloy wire, and
  controlling means for controlling the operation of said actuator according to a program, said program consisting in a sequence of a certain amount of actuations of said actuator per 24 hour time periods, or, in connection with provision of a timing means connected to said controlling means said program consisting in a sequence of actuations of said actuator that varies according to the time of day or, in connection with provision of a timing means connected to said controlling means and an input device for inputting data to said controlling means, adapting said controlling means so as to be programmable by means of said data, or adapting said program of said controlling means to comprise algorithms for automatically altering the sequence of actuations of said actuator according to input of data relative to the actual glucose level in the blood of the user of the device and/or intake of nutrients by said user.

Hereby, compliance is enhanced by providing a device with capabilities of rendering a very specific and well-tuned dosage which may be altered according to the specific development of the individual user.

So as to achieve a compact dispensing device, the pump means may comprise a piston rod for displacing a piston in a cylindrical container of said medicine to be dispensed and an actuator for displacing said piston rod, wherein said piston rod is configured such that the portion of said piston rod between said actuator and said piston is rectilinear and rest of said piston rod is arcuate, and such piston rod may comprise elements arranged in a row and interconnected by hinge elements, wherein each element is provided with a surface spaced from said hinge element and configured to abut a corresponding surface of an adjacent element when said piston rod is rectilinear, and said elements may be provided with screw threads on the outer surface thereof for co-operating with corresponding screw threads of the actuator.

In an alternative embodiment such piston rod may comprise a strip having an arcuate cross section taken transverse to the longitudinal direction of said strip which is rectilinear between said actuator and said piston while the rest of the strip is wound into a roll. The strip may be provided with apertures, preferably transversely extending slits, evenly spaced along the length thereof for receiving corresponding projections of said actuator.

In a yet further aspect, the invention relates provides a combination of a dispensing device as specified above and a programming controller, said dispensing device and said programming controller comprising co-operating transmission and/or receiving means for mutual communication of data, said programming controller preferably being a cellular telephone or a personal computer or a laptop computer or a hand held computer.

Moreover, the invention provides a method of controlling the operation of a disposable, wearable, self-contained medicine, particularly insulin dispensing device comprising
a housing,
an insulin source in said housing,
a pump means in said housing and adapted for pumping insulin from said insulin source to a catheter for injection of said insulin in a user of the device,
an actuator for said pump means, preferably an actuator comprising a shape memory alloy wire, and
controlling means for controlling the operation of said actuator according to a program,
said method comprising the steps of:
providing said controlling means with data for generating and/or amending said program prior to and/or after initiation of use of said dispensing device.

Furthermore, in a yet other aspect, the invention also relates to a method of controlling the operation of a disposable, wearable, self-contained medicine, particularly insulin dispensing device comprising
a housing,
an insulin source in said housing,
a pump means in said housing and adapted for pumping insulin from said insulin source to a catheter for injection of said insulin in a user of the device and, said catheter being associated with said housing and projecting generally perpendicularly to a generally planar surface of said housing intended for abutting a skin surface of a user of the device,
an adhesive layer provided on said planar surface for adhering said planar surface to said skin surface,
a combined microphone and loudspeaker associated with said housing, preferably arranged inside said housing,
recording and play back means connected to said combined microphone and loudspeaker and associated with said housing, preferably arranged inside said housing, such that verbal messages may be recorded and played back by said dispensing device, and
manual operating means for manually controlling the operation of said dispensing device
said method comprising the steps of:
recording verbal instructions in said recording means for instructing the user of the device in the operation of said dispensing device, and
playing back said verbal instructions.

Finally, the invention relates to a method of controlling the operation of a disposable, wearable, self-contained medicine, particularly insulin dispensing device comprising
a housing,
an insulin source in said housing,
a pump means in said housing and adapted for pumping insulin from said insulin source to a catheter for injection of said insulin in a user of the device and, said catheter being associated with said housing and projecting generally perpendicularly to a generally planar surface of said housing intended for abutting a skin surface of a user of the device,
an adhesive layer provided on said planar surface for adhering said planar surface to said skin surface,
a combined microphone and loudspeaker associated with said housing, preferably arranged inside said housing,
a programmable computing means associated with said housing, preferably arranged inside said housing, and
signal conversion means connected to said combined microphone and loudspeaker and associated with said housing, preferably arranged inside said housing, and adapted for converting received audio signals into input signals for said computing means and for converting output signals from said computing means to audio signals,
said method comprising one or more of the steps of:
transmitting audio signals to said microphone for controlling the operation of said dispensing device,
receiving audio signals from said loudspeaker for evaluating the operation of said dispensing device.

In the following, the invention will be described and explained more in detail in connection with various embodiments of an insulin dispensing device according to the invention shown, solely by way of example, in the accompanying drawings where:

BRIEF DESCRIPTION OF THE DRAWINGS

FIGS. 13, 14A-C, and 15 are schematic views illustrating a first embodiment of an actuator with a flexible piston rod according to the invention for use in a compact dispensing device according to the invention, FIG. 16 is a schematic isometric view illustrating a second embodiment of an actuator with a flexible piston rod according to the invention for use in a compact dispensing device according to the invention.

DETAILED DESCRIPTION

Generally speaking, although the device according to the invention is primarily intended for dispensing insulin, it may also be used for dispensing other medicinal substances such as pain-killers, anti-biotics and so on, such that whenever the term insulin is used herein, any other dispensable medicine is intended to be covered by the term insulin unless not applicable either by explicit indication or by implicit indication owing to the context wherein the term insulin is employed. Furthermore, it should be noted that when the term carpule is utilized, it is not in any way limited by the WIPO resolutions or any trademark interpretation but is used to denote any cartridge, container, ampoule etc. suitable for storing and dispensing medicinal compounds.

Figure 1:
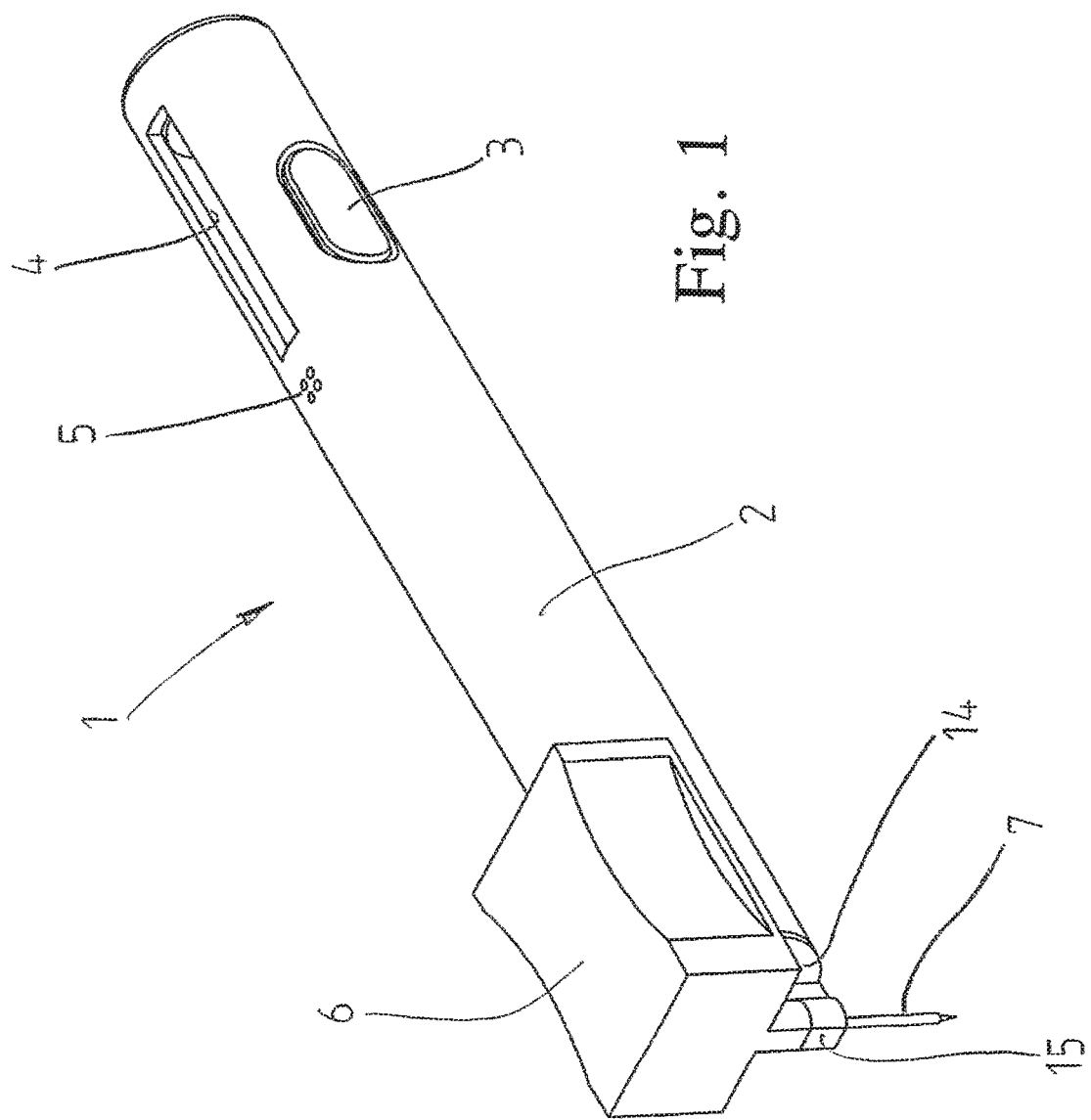
FIG. 1 is a schematic isometric view of a first embodiment of a disposable insulin dispensing device according to the invention before the adhesive pad for adhering the device to the skin of a user has been mounted on the device.

Referring now to FIG. 1, a disposable insulin dispensing device according to the invention, generally referenced by the numeral 1, comprises a water-tight generally cylindrical housing 2 provided with a push button 3 for activating and deactivating the device as well as for activating a so-called bolus operation as explained in the following.

The housing further comprises a transparent window 4 for inspecting the operation of the device and apertures 5 for transmission of sound waves as explained in the following.

At one end of the housing 2 there is provided a stiletto 6 having a sharp needle 7 extending through a catheter 8 connected to a not shown insulin container or carpule inside the housing 2 as explained in the following.

Figure 2:
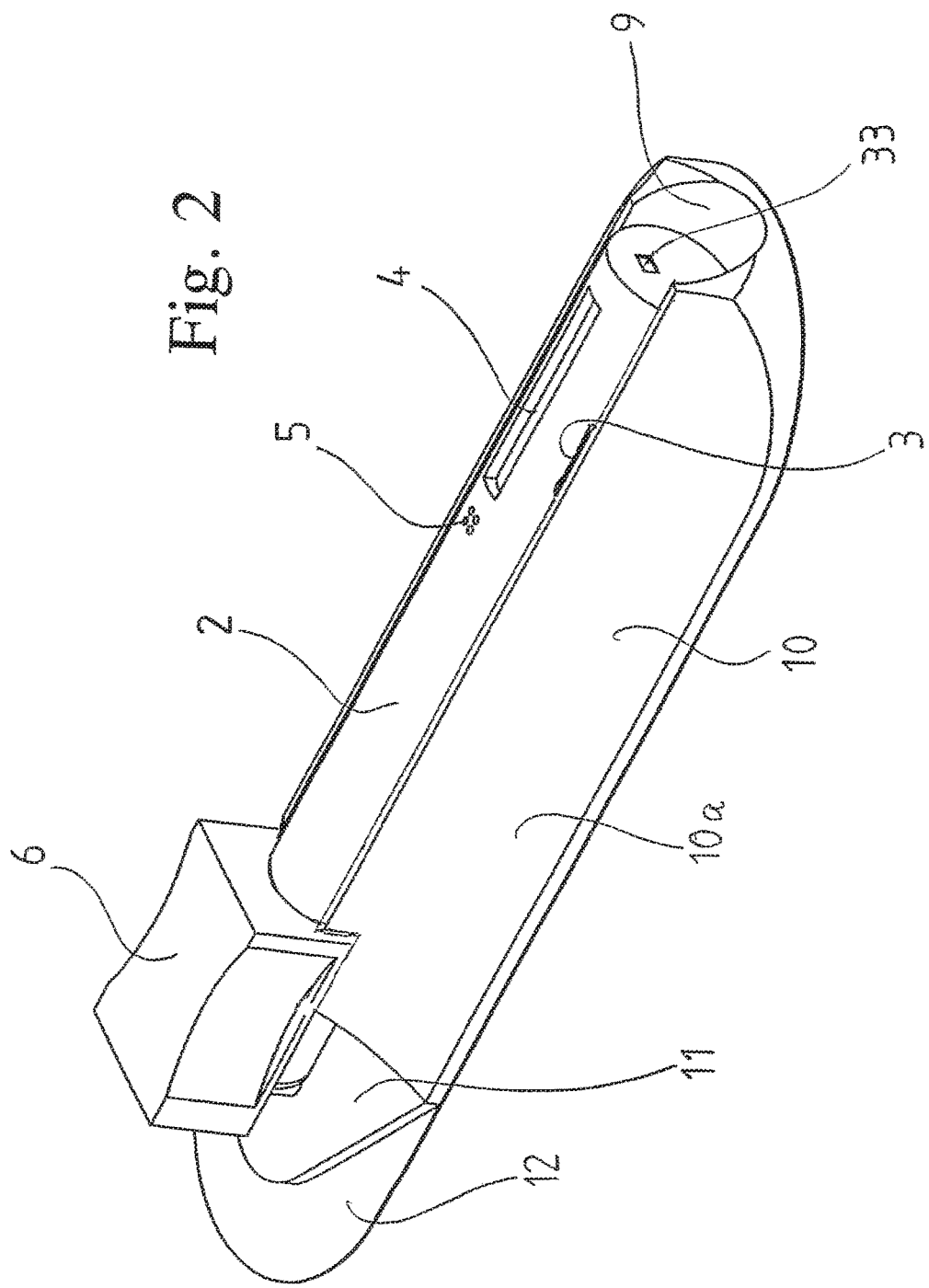
FIG. 2 is a schematic isometric view of the device of FIG. 1 seen from another angle and with the adhesive pad mounted thereon.
Figure 3:
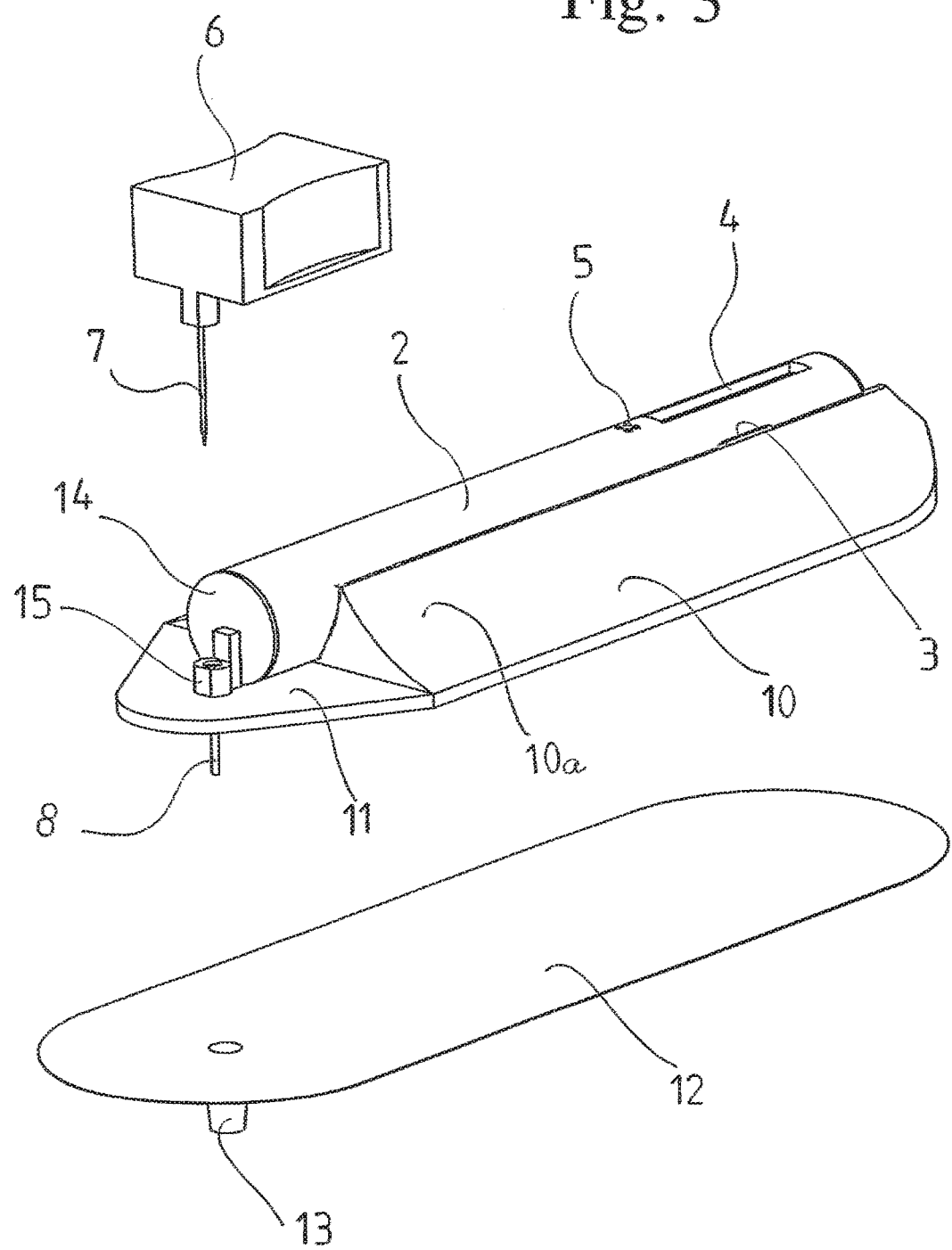
FIG. 3 is a schematic isometric partly exploded view of the device of FIG. 2.

Referring now to FIGS. 2-3, the housing 2 is fixedly received in a trough 9 of an adhesive pad 10 made of a combination of a plate 11 of skin-friendly adhesive material, for instance as well known in the field of ostomy pouches, see for instance European patent application no. 0413250 and European patent application no. 0092999, and a relatively compressible portion 10a made of foam material attached to the plate 11. The catheter 8 extends through the planar portion 11 of the pad 10. The push button 3 is protected by the foam material 10a so as to avoid inadvertent operation of the button for instance when the user is asleep.

A slip release film 12 is adhered to the bottom surface of the adhesive plate 11 for protecting the adhesive surface of the plate 11 such that the adhesive properties are intact when the pad is to be adhered to the skin of a user of the dispensing device. The release film 12 is provided with a protective hollow projection 13 for receiving the catheter 8 and the needle 7 of the stiletto 6 so that the needle 7 and the catheter 8 are protected by the projection 13 before use of the dispensing device 1. The housing 2 is provided with an end cover 14 on which the catheter 8 is mounted by means of a communication bushing 15 provided with an internal elastomeric mass (not shown) and a communication passage for communicating the catheter 8 with the interior of the housing 2 as explained in the following in connection with FIG. 4.

In use, the user removes the protective release sheet 12 thereby exposing the tip of the needle 7 such that the needle may be inserted subcutaneously at the same time that the adhesive pad 10a, 11 is adhered to the abdominal skin of the user. When the needle 7 and the catheter 8 have been inserted subcutaneously and the device has been adhered to the skin of the user, the stiletto 6 is removed whereby communication is established between the catheter 8 and the interior of the housing 2 for supplying insulin subcutaneously to the user of the device.

The elastomeric mass in the bushing 15 seals the exit opening of the needle 7 when it is removed such that no insulin may leak through said exit opening but is constrained to flow solely from the carpule to the catheter 8.

Figure 4:
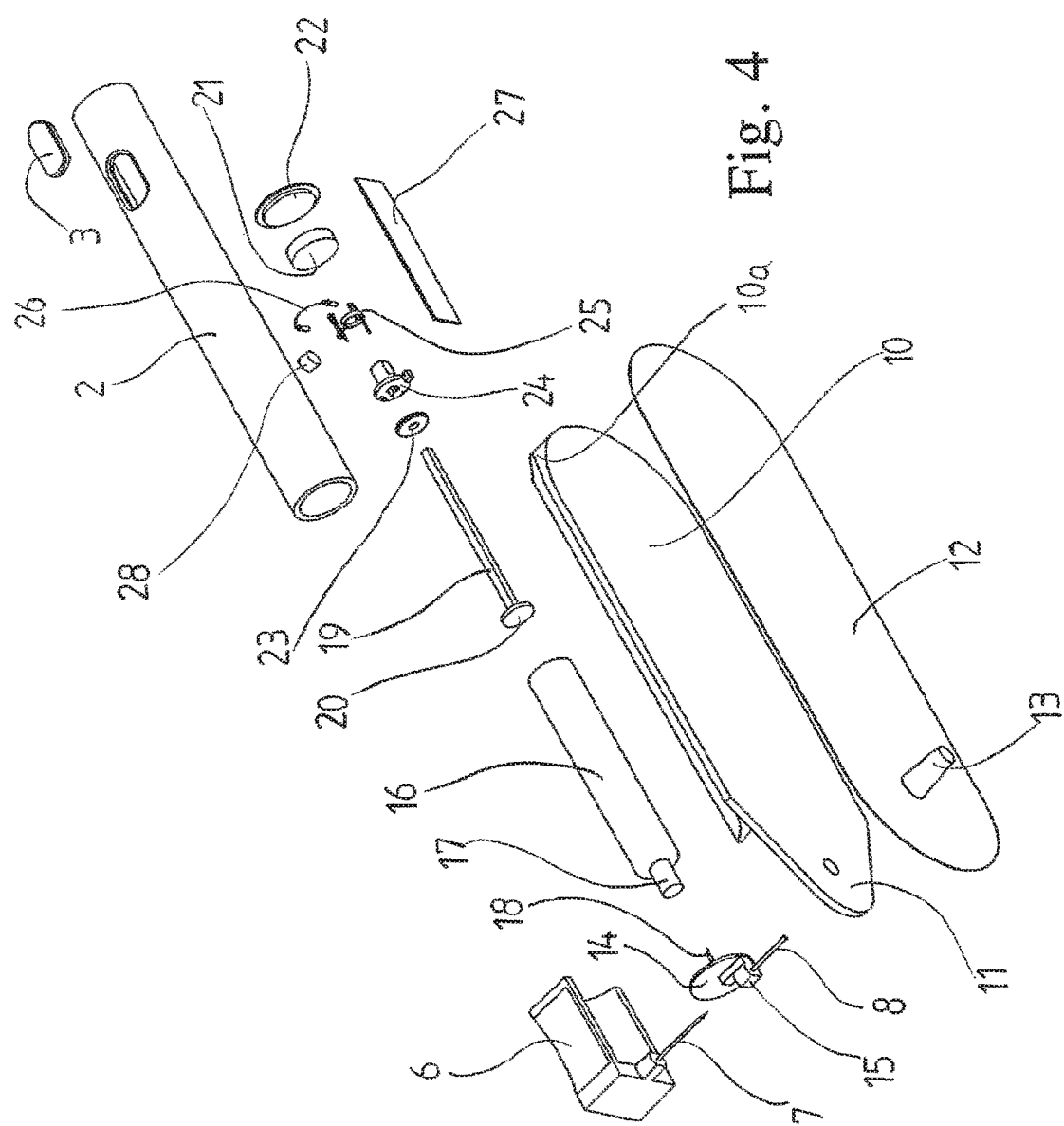
FIG. 4 is a schematic entirely exploded view of the device of FIG. 2.

Referring now to FIG. 4 showing an exploded view of the components of the insulin dispensing device according to the invention, the housing 2 contains a container or a carpule 16 for storing and dispensing insulin. The container or carpule 16 is of a well-known type having a perforatable dispensing projection 17 for receiving a catheter 18 for communicating the interior of the container 16 with the catheter 8 through the communication bushing 15 when the needle 7 has been retracted from said elastomeric mass inside the bushing 15 as explained above.

A spindle 19 provided with a piston 20 is received in the container 16 such that axial displacement of the spindle towards the dispensing projection 17 will press insulin through the catheter 18 to the catheter 8. The spindle 19 is rotated and displaced by means of a shape memory alloy actuator described more in detail in the following with reference to FIG. 6.

A battery 21 for supplying power to the shape memory actuator is provided adjacent an end cover 22 of the housing 2.

The shape memory actuator comprises a pawl or ratchet wheel 23, a guide bushing 24, a spring wheel 25 and a shape memory wire 26. The operation of the shape memory actuator will be described more in detail in the following with reference to FIGS. 6 and 7.

A printed circuit board 27 is provided for controlling the function of the dispensing device and the various operational steps thereof as described in the following.

Finally a combined microphone/loudspeaker 28 is arranged inside the housing 2 adjacent the apertures 5 for receiving and emitting sound waves for the purposes described below.

Figure 5:
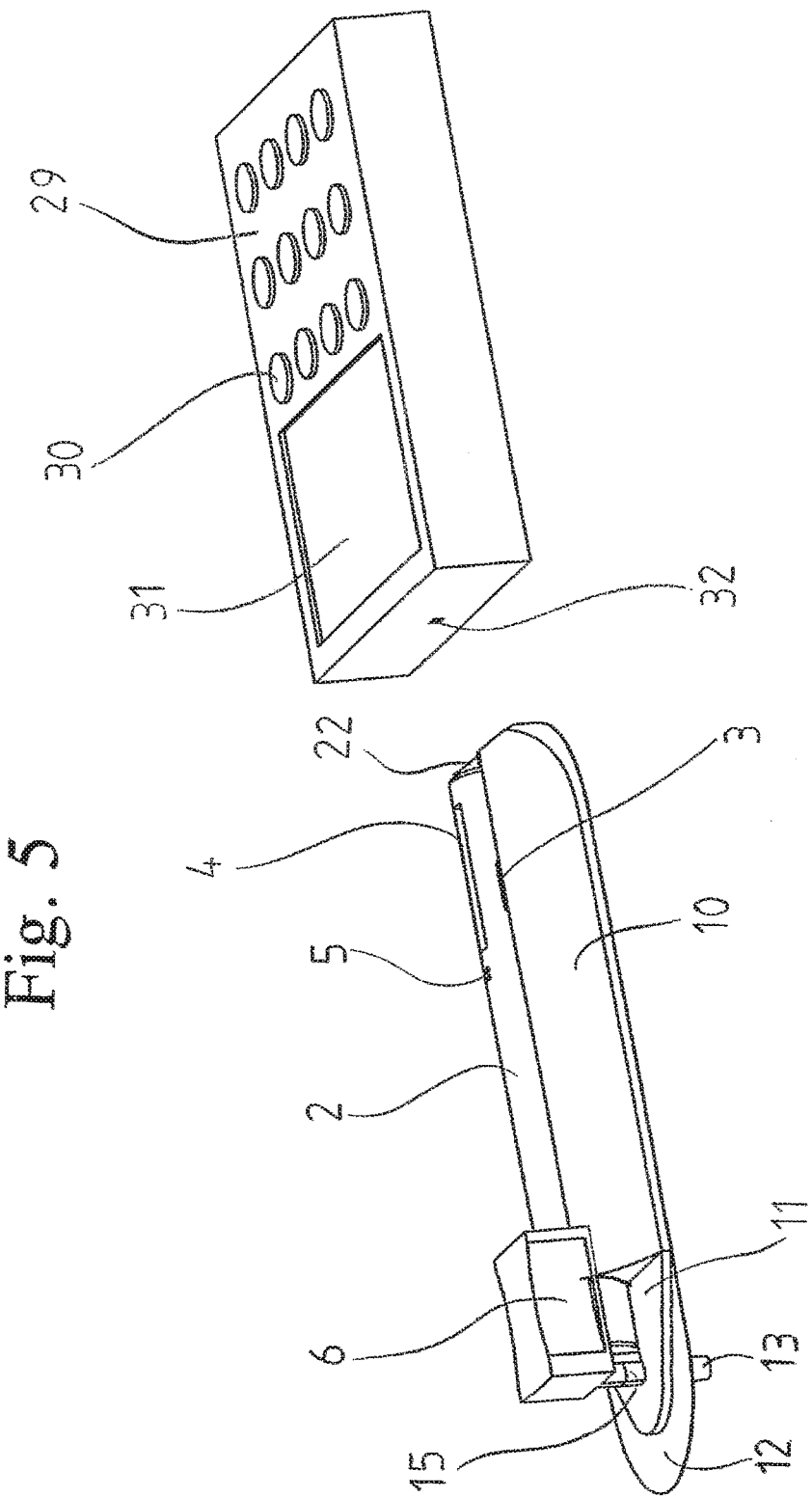
FIG. 5 is a schematic isometric view of the device of FIG. 2 together with a programming device according to the invention.

Referring now to FIG. 5, a programming device or controller 29 having programming keys 30 and a display 31 is shown proximate the dispensing device for communicating with a not shown receiver/transmitter arranged inside the housing 2. The communication may take place by infra red signals or other suitable signals transmitted from and to an opening 32 leading to a transmitter/receiver inside the controller 29 to and from, respectively an opening 33 (see FIG. 2) in the end cover 22 of the housing 2 leading to said not shown transmitter/receiver inside the housing 2.

Figure 6:
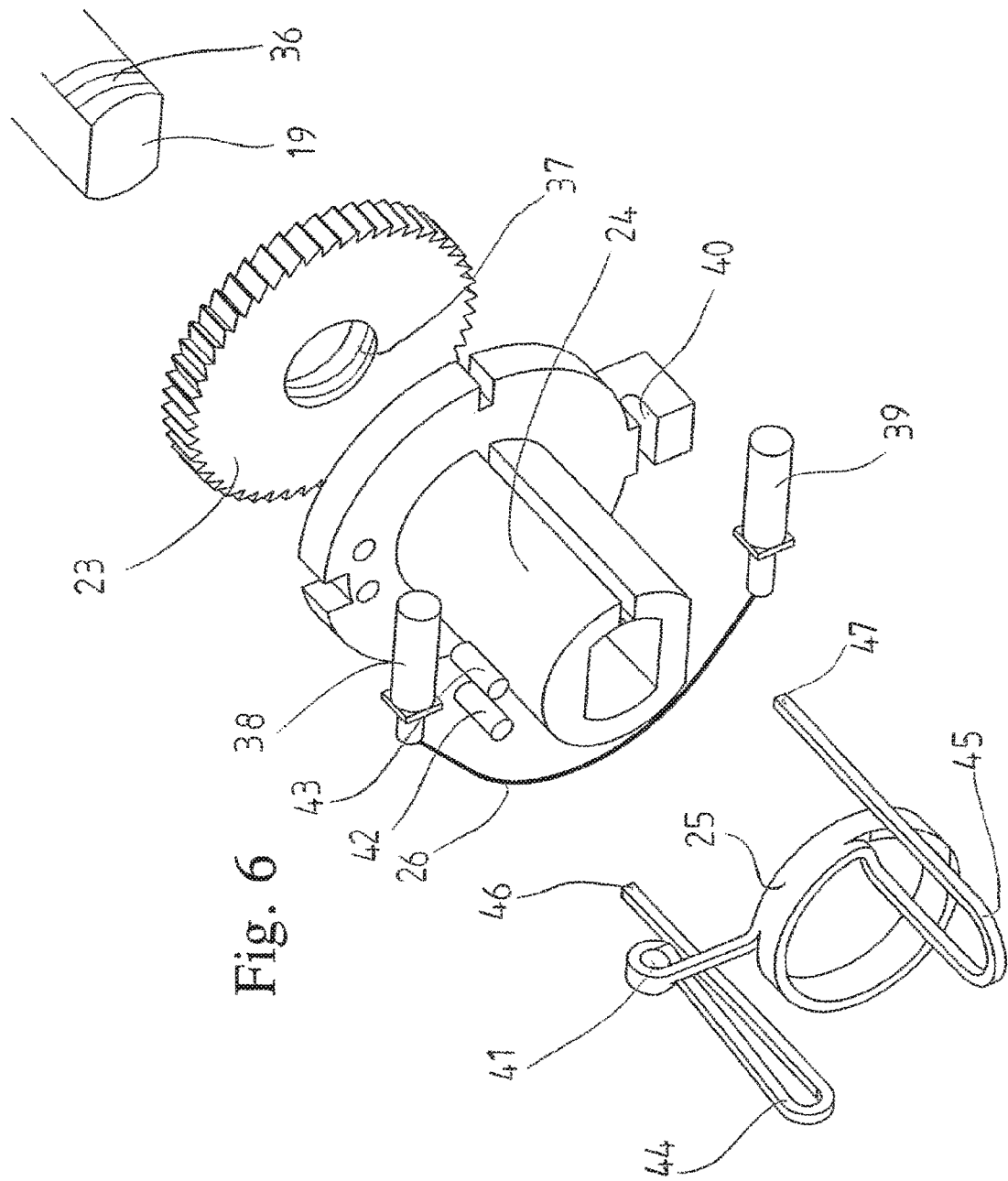
FIG. 6 is a schematic enlarged scale exploded view of a shape memory alloy actuator mechanism according to the invention of the device of FIG. 2.
Figure 7:
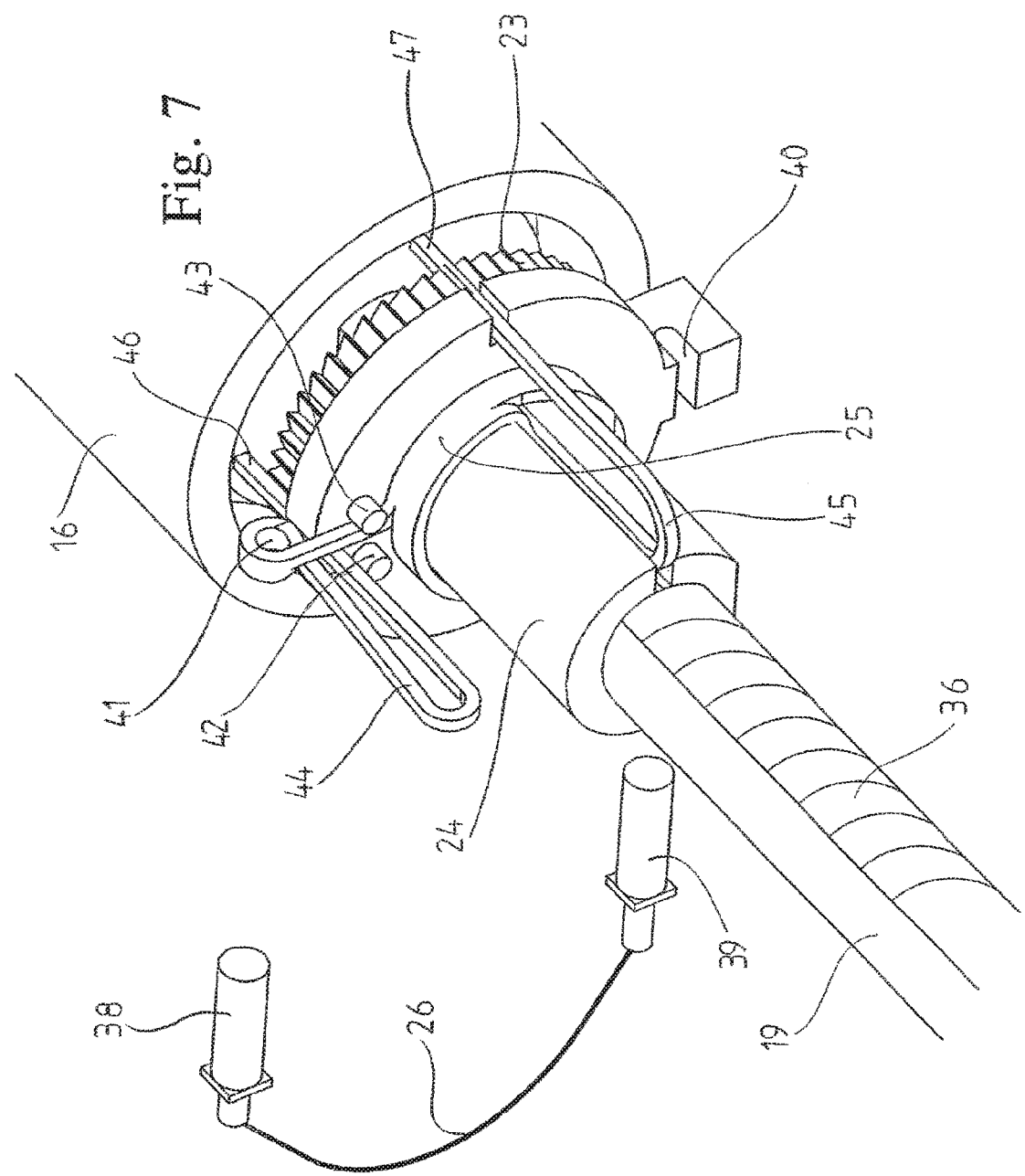
FIG. 7 is a schematic view corresponding to FIG. 6 with the elements of the shape memory actuator shown in interconnected operative relative positions.
Figure 8:
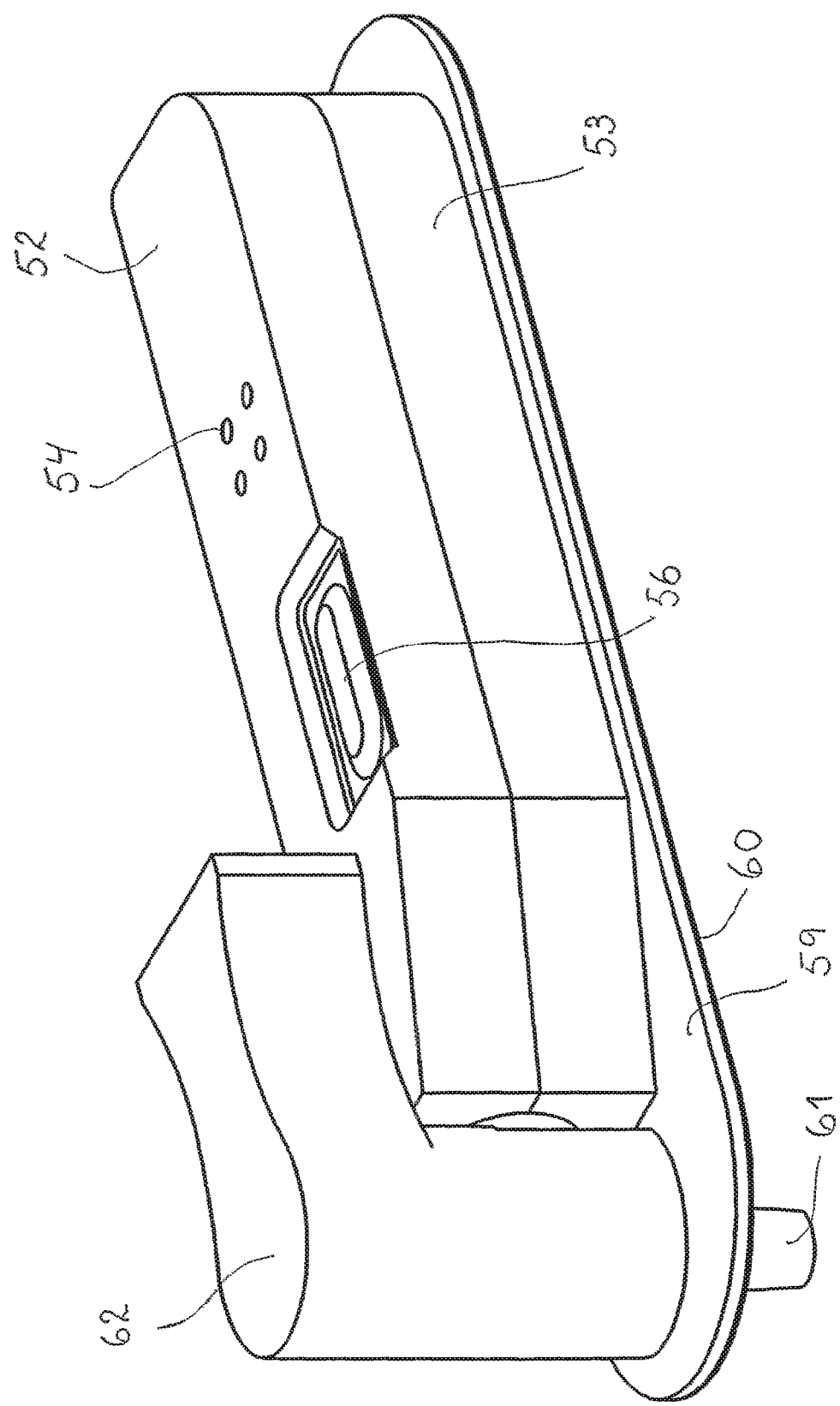
FIG. 8 is a schematic isometric view of a second, more compact embodiment of a disposable insulin dispensing device according to the invention.
Figure 9:
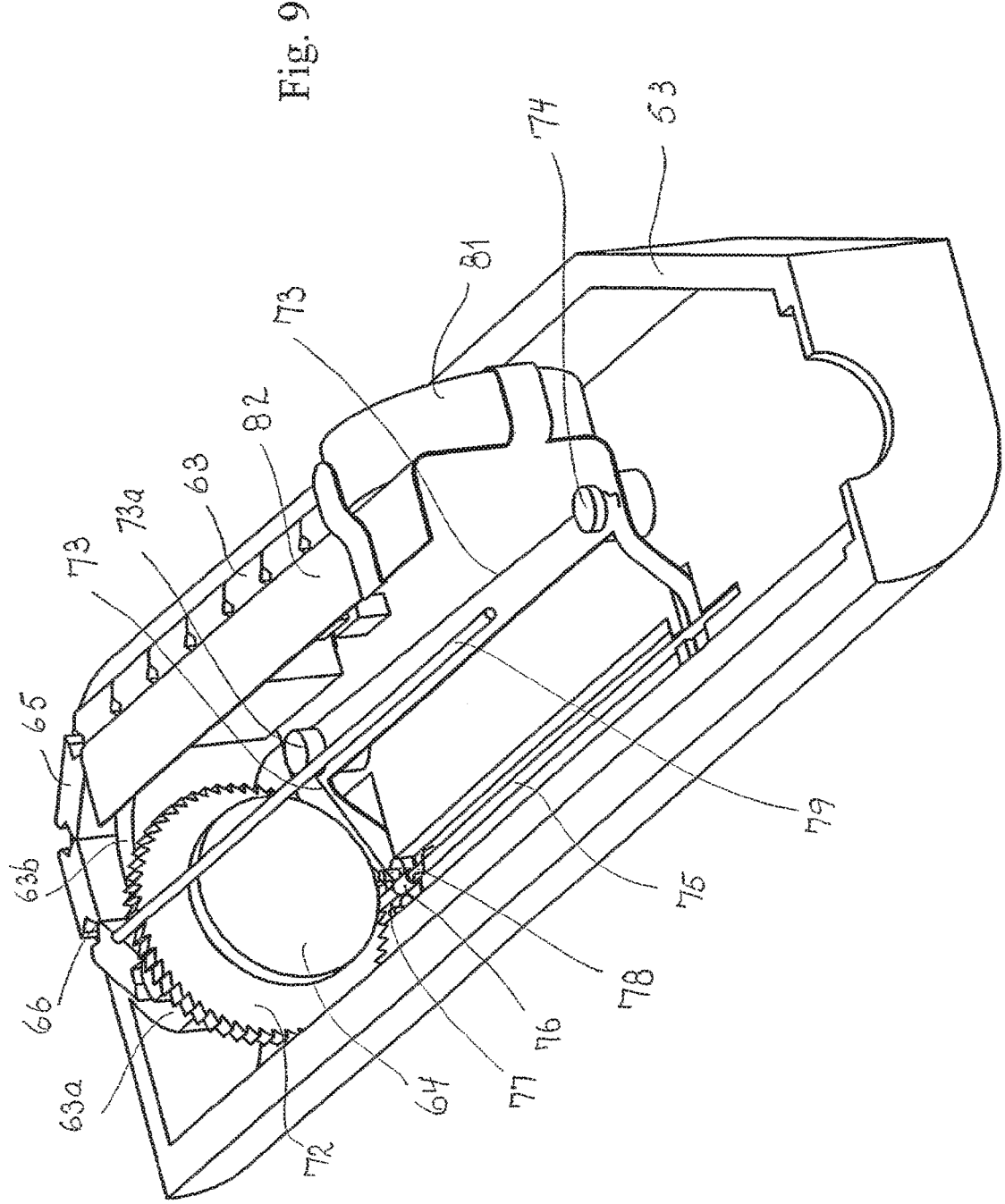
FIG. 9 is a schematic, isometric view of the device of FIG. 8 with the top removed so as to illustrate the co-operating elements of the device.
Figure 10:
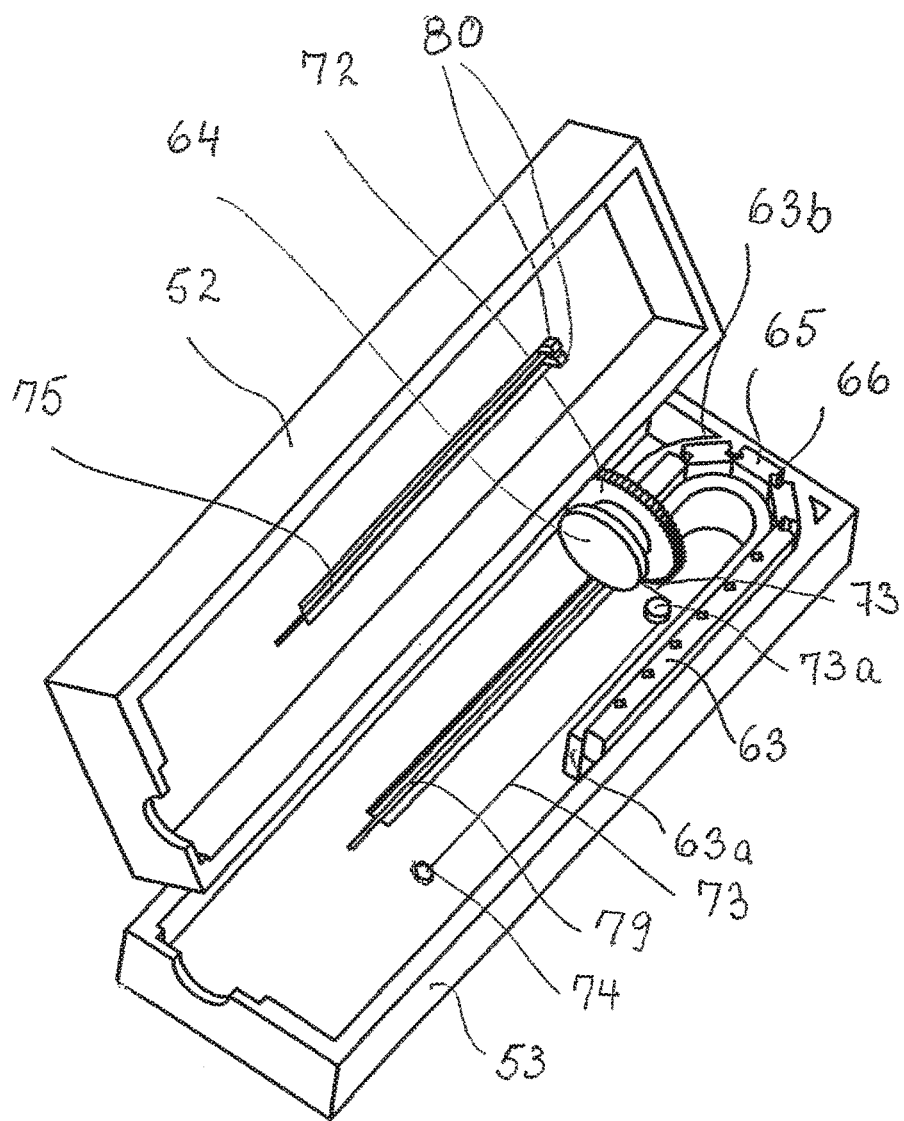
FIG. 10 is a schematic, isometric view of the device of FIG. 8 seen from another angle than FIG. 9.
Figure 11:
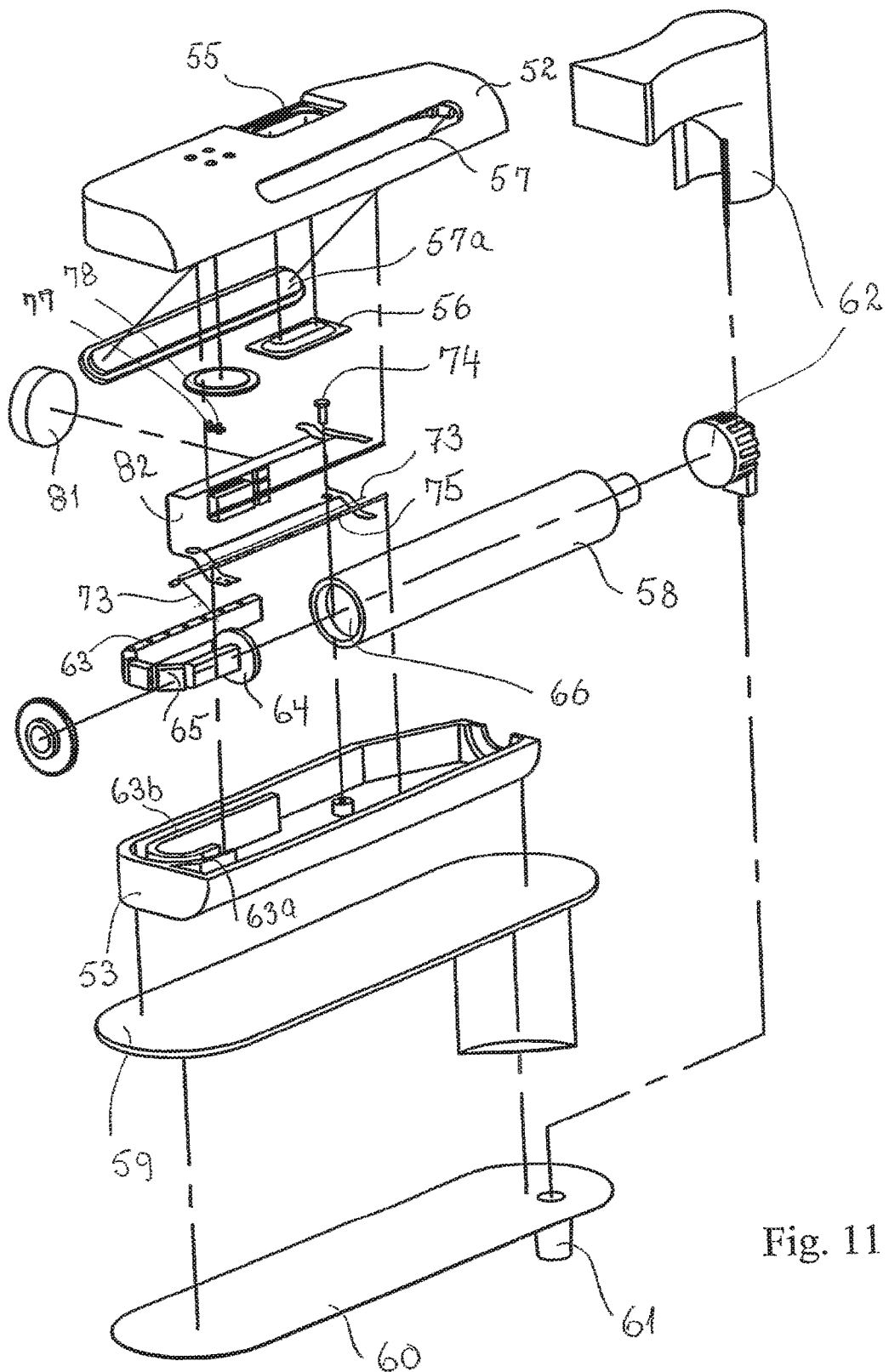
FIG. 11 is a schematic exploded view of the device of FIGS. 8-10, FIGS. 12a-12c are very schematic views, seen in the direction of the axis of the carpule, of the operation of the drive mechanism of the device of FIGS. 8-11 illustrating the interaction of the pawl or ratchet wheel with the spring elements and the shape memory alloy wire.

Referring now to FIGS. 6 and 7, the spindle 19 is displaced axially in the direction of the arrow R1 by counterclockwise rotation of the pawl wheel 23 in the direction of the arrow R2 whereby the thread 36 meshing with the internal thread 37 results in said axial displacement whereby the piston 20 is displaced further into the carpule 16 to dispense insulin through the catheter 18 to the catheter 8 (FIG. 4).

Rotation of the pawl wheel 23 is accomplished by means of the shape memory alloy (for instance Nitinol) wire 26 attached to electrically conductive rods 38 and 39 that are fixed in recesses 40 and 41, respectively, in the electrically non-conductive guide bushing 24 and the electrically conductive spring wheel 25, respectively.

The recess 40 is provided with not shown electrical contacts for electrically connecting the rod 39 to the battery 21 for supplying electrical current to the shape memory alloy (SMA) wire 26 to heat it in a manner and sequence controlled by the program elements in the printed circuit board 27.

The spring wheel 25 has U-shaped spring arms 44 and 45 for exerting a spring force on the ends 46 and 47 thereof, respectively, in a direction towards the center of the pawl wheel 23 such that the ends 46 and 47 are constantly biased to enter into engagement with the teeth of the pawl wheel 23.

The stop pins 42 and 43 are electrically connected to the printed circuit board 27 for emitting an electrical signal thereto when the spring wheel arm 48 contacts said stop pins.

The rod 38 is as mentioned above electrically connected to the power source such that an electrical current may be passed through the rod 38, the wire 26, the rod 39, the loop recess 41 and the spring wheel 25 to heat the wire 26 to cause the wire to contract and rotate the pawl wheel the distance of one tooth in the direction of arrow R2 by means of the arm end 46 engaging a tooth of the wheel until the arm 48 contacts the stop pin 42 that emits a signal to the control printed circuit board 27 whereby the current through the wire 26 is interrupted and the SMA wire 26 cools off and expands.

The other arm end 47 engages a tooth of the wheel 23 as a pawl and prevents the wheel 23 from rotating clock-wise. The spring effect of the spring wheel 25 in the tangential direction causes the arm 42 to move back into contact with the stop pin 43 thereby tightening the expanded SMA wire 26.

The signals from the stop pins 42 and 43 are also utilized to indicate correct functioning of the pump and as an indication of the number of doses administered through the catheter 8.

Referring now to FIGS. 8-12, a second, more compact, embodiment of a medicine pump 51 according to the invention comprises a housing upper portion 52 and a housing lower portion 53, the upper portion 52 having audio apertures 54 for allowing audio signals to travel relatively unencumbered through the wall of the upper portion 52 from and to an audio element 54a, a bolus button aperture 55 for allowing depression of a bolus button 56 and an inspection aperture 57 covered by a transparent element 57a for allowing monitoring of the contents of an insulin carpule 58 provided inside the housing.

The lower housing portion 53 is adhered to an adhesive pad 59 covered by a release sheet with a needle protection projection or indentation 61 very similar to the corresponding elements of the embodiment of FIGS. 1-4. The carpule 58 co-operates with a catheter/stiletto assembly 62 in the same manner as described in connection with the embodiment of FIGS. 1-4.

The embodiment of FIGS. 8-12 is very similar in construction and in operation to the embodiment of FIGS. 1-4 with the exception of the rigid rectilinear spindle or piston rod 19 being substituted by a flexible piston rod 63 according to the invention and the design of the shape memory alloy wire actuator as will be described in the following.

Figure 13:
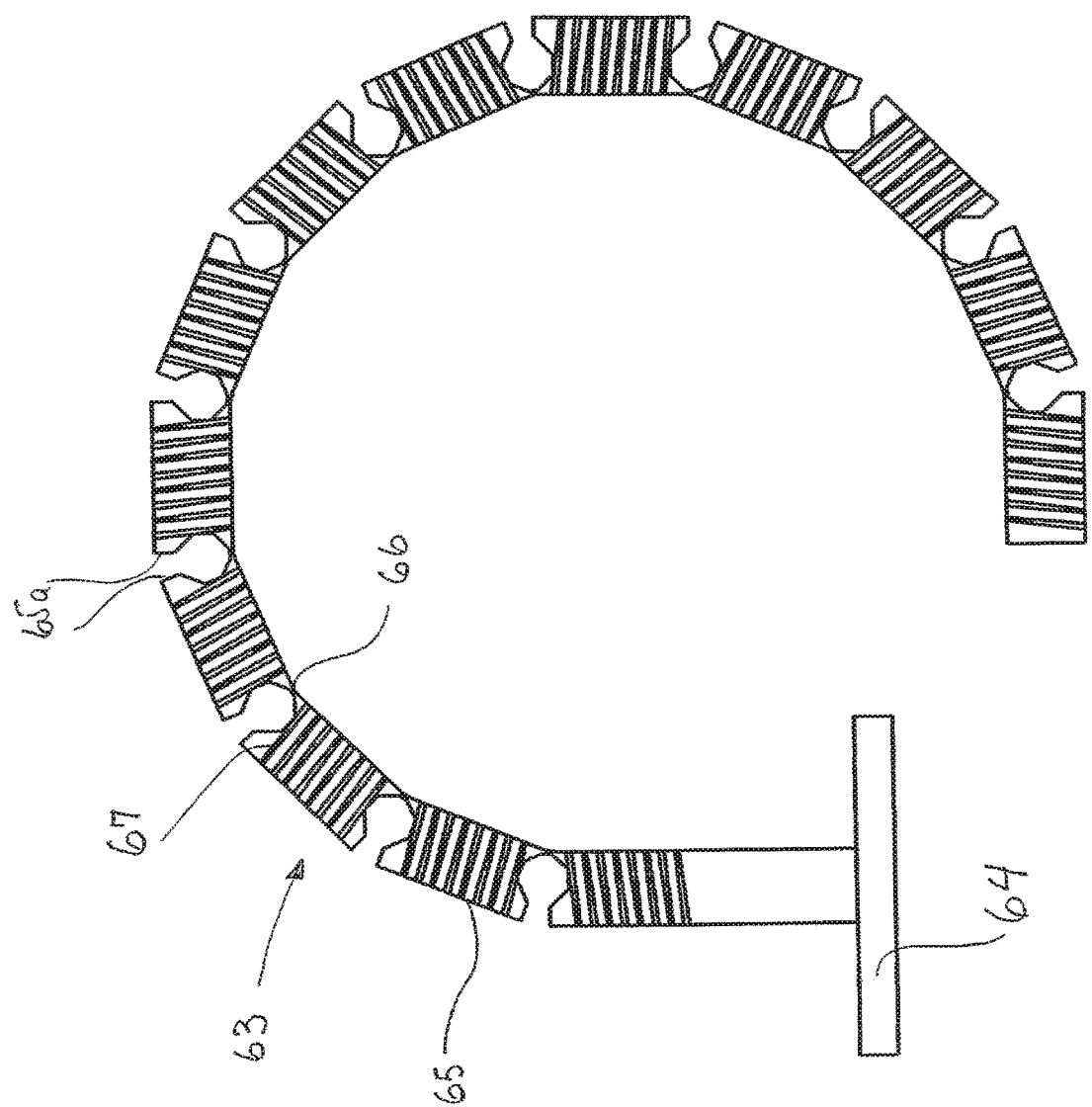
Figure 14C:
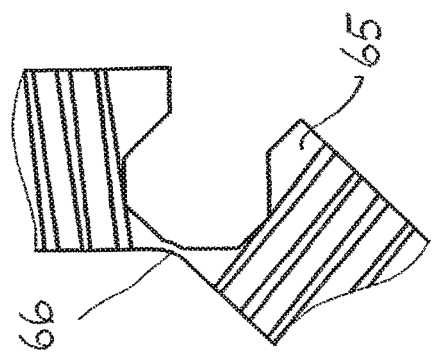

A piston 64 corresponding to piston 20 of FIG. 4 is attached to one end of a flexible piston rod 63 constituted by a series of elements 65 interconnected by hinge means 66 (see FIGS. 13-15) and arranged for movement between two guide walls 63a and 63b. The piston 64 abuts a displaceable wall or piston 66 of the carpule 58 such that axial displacement of the piston 64 will press insulin out of the carpule 58 into the catheter assembly 62.

Figure 14B:
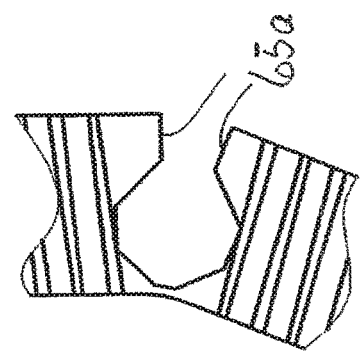
Figure 14A:
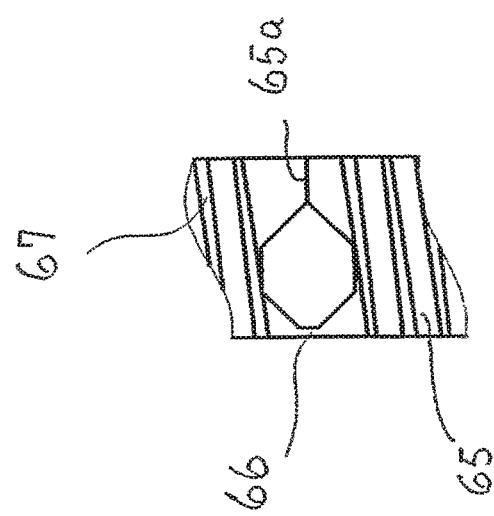

The elements 65 are integral with each other by means of hinges 66 which allow adjacent elements to pivot relative to one another from the position abutting one another shown in FIG. 14a wherein the elements 65 together form a rectilinear piston rod with abutment surfaces 65a and hinges 66 affording rigidity and thus rendering the piston rod 63 capable of exerting a pressure on the piston 66 of the carpule without laterally deflecting, to the position shown in FIG. 14b wherein the elements are pivoted way from one another so as to allow the curvature of the piston rod 63 which allows the compact configuration of the device with the initially major part of the piston rod extending along the length of the carpule 68.

The material of the flexible piston rod 63 is any suitable moldable material, but it is preferred that the material is a plastic material such as Nylon or POM because of cost and re-cycling issues.

Each element 65 is provided with exterior threads 67 on two opposed portions 69 and 70 of the elements having a circular cylindrical configuration for allowing an internal thread 71 of a pawl or ratchet wheel 72 (FIG. 12) to mesh therewith such that rotation of the pawl wheel 72 will displace the piston rod 63 into the carpule 58. At least the side of the elements 65 coinciding with the hinges 66 is flat to allow practical molding of the hinge. The flat side or flat opposed sides also allows preventing rotation of the piston rod 63 around its axis when being axially displaced by the internal thread 71 of the pawl wheel 72

The pawl wheel 72 is rotated by a shape memory alloy actuator comprising a wire 73 of a shape memory alloy such as Nitinol, one end of which is attached to a rivet 74 and the other end of which is attached to the free end of an actuator spring rod 75 by means of a crimp 76. The wire 73 extends around a pin 73a for change of direction. The free end of the actuator spring rod 75 is located such that it meshes with the teeth of the pawl wheel 72 and is biased by the spring force of the rod to exert a spring force in the tangential direction (arrow R1) and in the radial direction (arrow R2). Two end stop pins 77 and 78 limit the tangential movement of the actuator spring rod end 75.

A pawl spring rod 79 is located such that the end thereof meshes with the teeth of the pawl wheel 72 and is biased to exert a spring force in the radial direction (arrow R3). This end of the pawl spring rod 79 is constrained to substantially only move in the radial direction by two stop pins 80.

A battery 81 supplies power to the ends of the nitinol wire 73 for heating it so as to cause it to contract. The battery 81 is connected to the rivet 74 and the crimp 76 through a flexible printed circuit film 82 on which is incorporated the control circuits necessary for any programmed sequence of heating and cooling of the wire 73 as well as any other electronically controlled functions of the device.

Figure 12A:
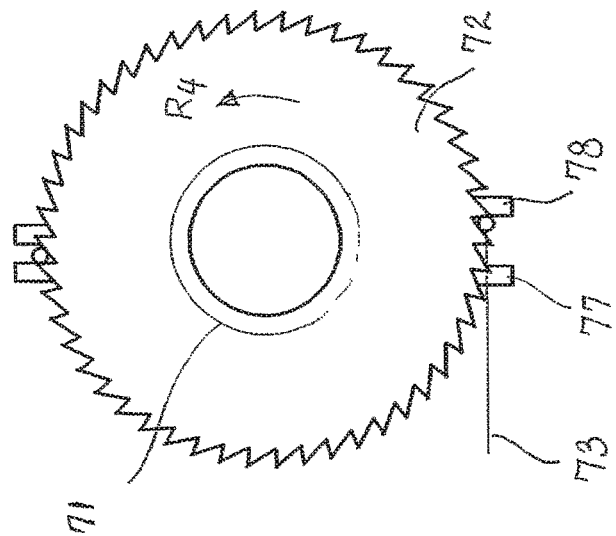
Figure 12B:
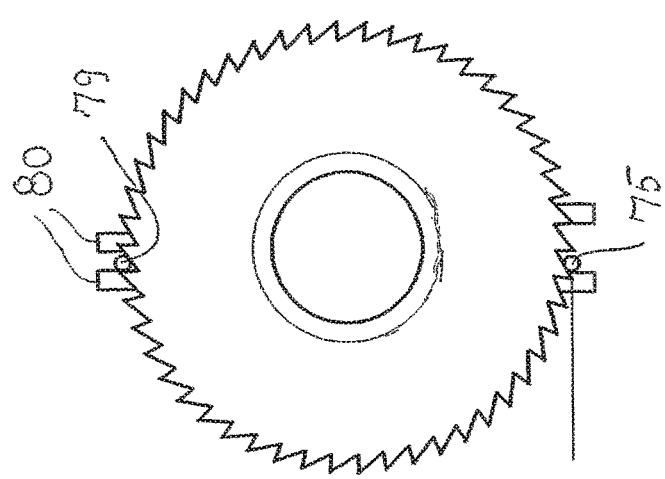
Figure 12C:
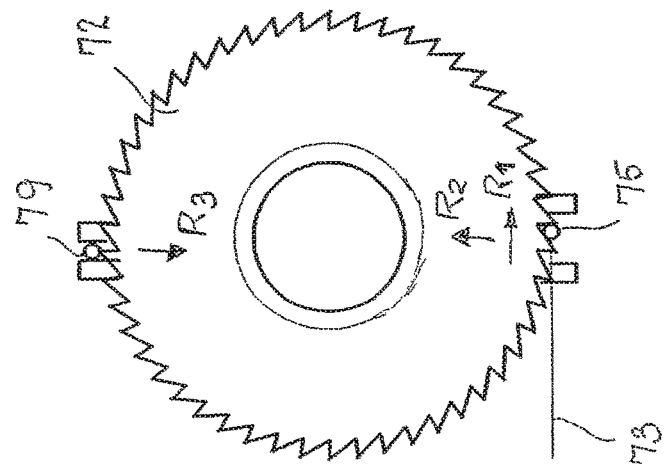

Rotation of the pawl wheel 72 in the counter clock-wise direction of the arrow R4 is brought about as illustrated in FIGS. 12a-12c. In FIG. 12a the wire 73 is cool and expanded so that the actuator spring rod end 75 is in its rightmost position abutting end stop pin 78. The pawl spring end 79 locks the pawl wheel 72 against clock-wise rotation.

In FIG. 12b the nitinol wire 73 has been heated and has contracted thereby pulling the actuator rod end 75 to the left against the spring forces R1 and R2 until it abuts the end stop pin 77.

In FIG. 12c the nitinol wire 73 has been cooled and the actuator spring rod end 75 is rotating the wheel 72 counter clock-wise until abutting end stop pin 78 again while the pawl rod end is ratcheting against the spring force R3. Hereby, the pawl wheel has been rotated the peripheral distance of one tooth thereof.

As the pawl wheel rotates, the internal thread 71 of the wheel meshing with the threads 67 of the flexible piston rod elements 65 displaces the piston rod 63 into the carpule 58 for dispensing insulin through the catheter 62.

The end stop pins 77 and 78 are electrically connected to the flexible print board film 82 so that monitoring of the correct function of the actuator may take place by registering electrical contact between the end stop pins 77, 78 and the spring rod end 75 which indicates correct functioning of the actuator.

The flexible piston rod 63 could also be displaced by means of another actuator, for instance such as described in connection with the embodiment of FIGS. 1-4.

Referring now to FIG. 16, a carpule 58 identical to the one described in connection with FIGS. 8-11 is located adjacent an actuator generally referenced by the numeral 90 with a piston 91 of the actuator abutting the not visible piston 66 of the carpule.

The piston 91 is attached to the end of a steel strip 92 having an arcuate cross section taken at right angles to the longitudinal direction of the strip. This arcuate shape entails a rigidity of the strip 92 against lateral deflection such that the strip can transmit pressure forces to the piston 91 without collapsing because of lateral deflection.

A row of evenly spaced elongate apertures 93 are provided in the strip 92 for receiving ribs 94 of a roller 95 having a gear 96 meshing with a worm gear 97. The worm gear is actuated by an actuator that may be similar to the shape memory alloy actuators of FIG. 6-7 or 8-12.

By rotating the worm gear 97 the gear 96 and roller 95 are rotated whereby the ribs 94 received in the slits 93 unwind the strip 92 from the roll and displace it into the carpule whereby the piston 91 displaces the carpule piston and dispenses the insulin from the carpule 58 that is located in the dispensing device in the same manner as the carpule 58 of FIGS. 8-12.

A medicine dispensing device or insulin pump according to the invention may function in several different manners depending on the design and programming of the various control elements of the circuit board 27:

1. Stand alone pump with constant flow:

The pump functions as a constant flow pump and may be designed for different flow rates, for instance 20 units/24 hours, 30 units/24 hours, etc. By depressing the bolus button 3 and holding it down, the pumping program is initiated and by again pressing the button 3 down and holding it, the pumping program is terminated while a short duration pressure on the bolus button 3 activates a bolus additional dosage of insulin of a certain magnitude.

Figure 17:
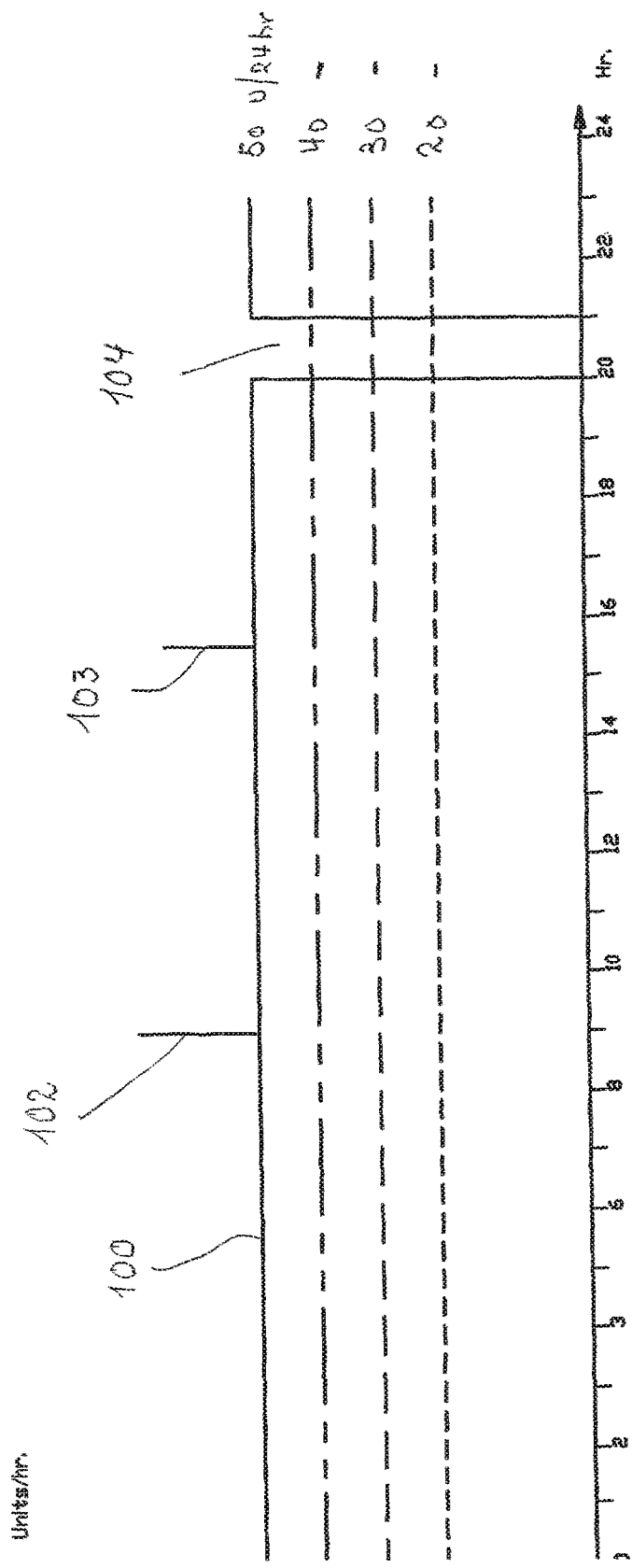
FIGS. 17-19 are graphs illustrating different insulin dispensing programs.

FIG. 17 illustrates a possible programming of this type with the line 100 indicating a constant flow corresponding to 50 units/24 hr with a flow pause indicated at 101 between 20 and 21 hours after start. Bolus extra dosages are indicated at 102 and 103. Other flow rates are indicated with broken line graphs.

2. Stand alone pump with varying flow:

A timing device is incorporated in the printed circuit board 27 so that a standard program controls the flow dispensed by the pump during recurring 24 hour periods. The pre-programmed operating instructions may for example result in a lower dosage at night than during the day and an extra dosage at mealtimes.

Figure 18:
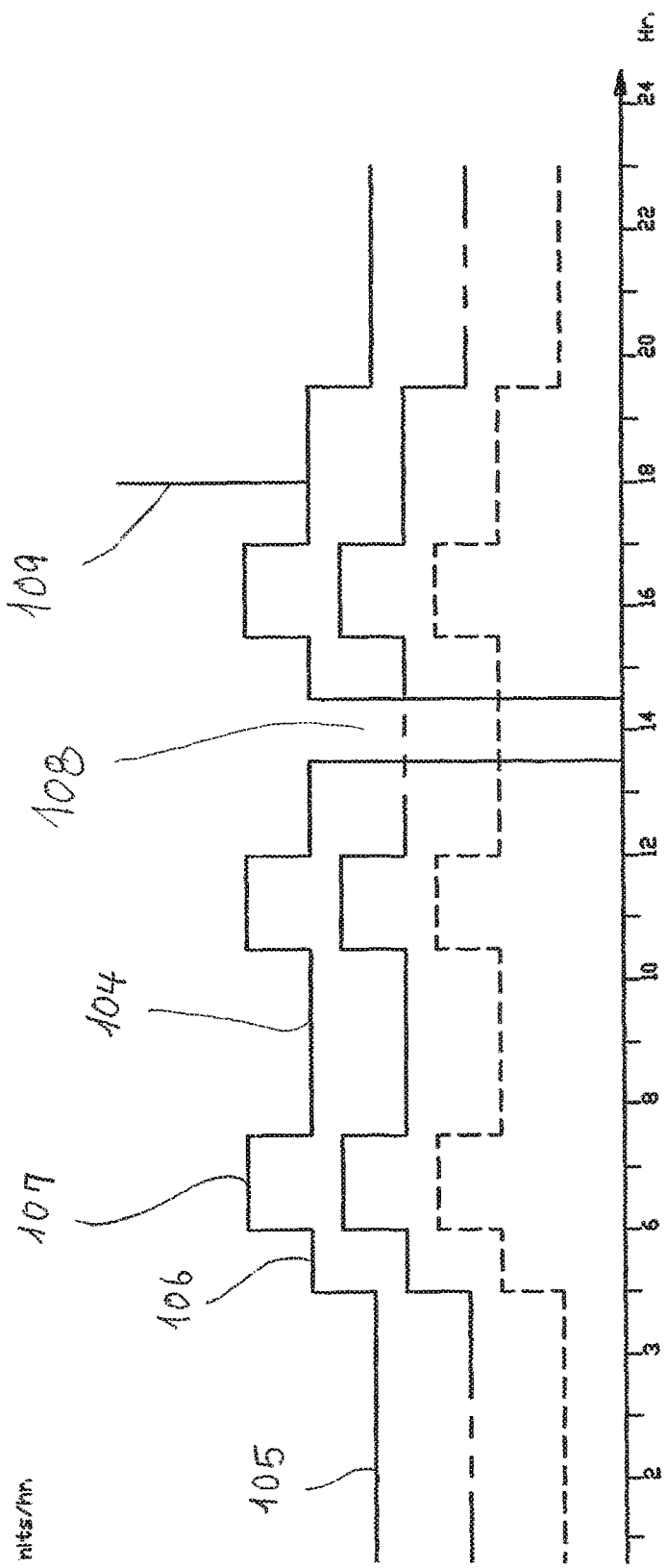

FIG. 18 illustrates a possible programming of this type with the graph 104 indicating night-time dosage 105, day-time dosage 106, meal-time dosage 107, dosage pause 108 and bolus 109. Other dosage programs are indicated in broken lines.

3. Programmable pump type 1:

The pump is not provided with a predetermined program, but is provided with a programmable unit in the printed circuit board 27 and can be programmed by the user or a doctor by means of a controller 29. The programming must be able to take place through the packing material in which the dispensing device is supplied so that the user can transport the device in a sterilized packaging on vacations or the like without having to carry the controller along. The controller is a dedicated unit that for instance via a USB plug can be connected to a PC or it can be provided with cellular telephone capability for transmission of data. The controller can thus be programmed by a doctor or a user and be used for programming of the functioning of all subsequently used disposable dispensing devices.

4. Programmable pump type 2:

This pump functions in the same manner as programmable pump type 1, but the controller is a personal data device such as the type marketed under the trademark PALM PILOT®, or a laptop PC. This gives the additional advantage that the user may input health information and glucose level measurement results directly into the controller or programming unit and thus communicate such information to the doctor who may use this information when deciding whether the programming function of the controller or the programming unit is to be altered for subsequently used disposable dispensing devices.

5. Programmable pump with audio input and output:

By providing the dispensing device with the microphone/loudspeaker 28 and a suitable recording/play-back chip in the printed circuit 27, short messages may be recorded by the dispensing device, and the short messages may be emitted by the device upon suitable manipulation of the bolus push button 3 or a separate recording button (not shown) mounted on the housing 2.

By means of this audio capability the user may record verbally formulated information regarding glucose levels, meal composition, exercise, etc. A timer may record the timing of each recorded message. A doctor may then use these recorded messages together with information about number and timing of bolus dosages, pumping stops and the program utilized for the dispensing of the insulin so as to evaluate the treatment and decide upon any changes in the programming and instructions to the patient which may be recorded by the doctor via a mobile telephone or the like such that messages are automatically delivered to the user at predetermined times. Such a message could for example be 'remember to measure your glucose level' (message program to be delivered by the dispensing device to the user each morning at 8 o'clock) and so on.

Furthermore, standard instructions can be included in the programming circuit so that the pump may deliver verbal messages to the user instead of audio signals such as beep sounds. The message could for instance be: 'Pump is stopped' or 'This is your third bolus in a row and you have taken a total of eight bolus dosages today' or 'The pump will be empty in two hours' and so on. Generally speaking, the audio capability described above will render the dispensing device provided with such capability much more user-friendly, especially for users initiating a treatment or not very disciplined as regards compliance.

6. Closed loop re-programmable pump:

Either the controller or the computing unit mounted in the printed circuit 27 may be programmed to react to information regarding actual glucose blood level inputted by the user perhaps together with other information, such as data regarding the timing and constitution of the last meal, to alter the program of the dispensing flow or dosage to take into consideration this information such that the dispensing device to a certain extent constitutes a closed loop, fuzzy logic, semi-automatic self re-programming insulin dispensing device.

Figure 19:
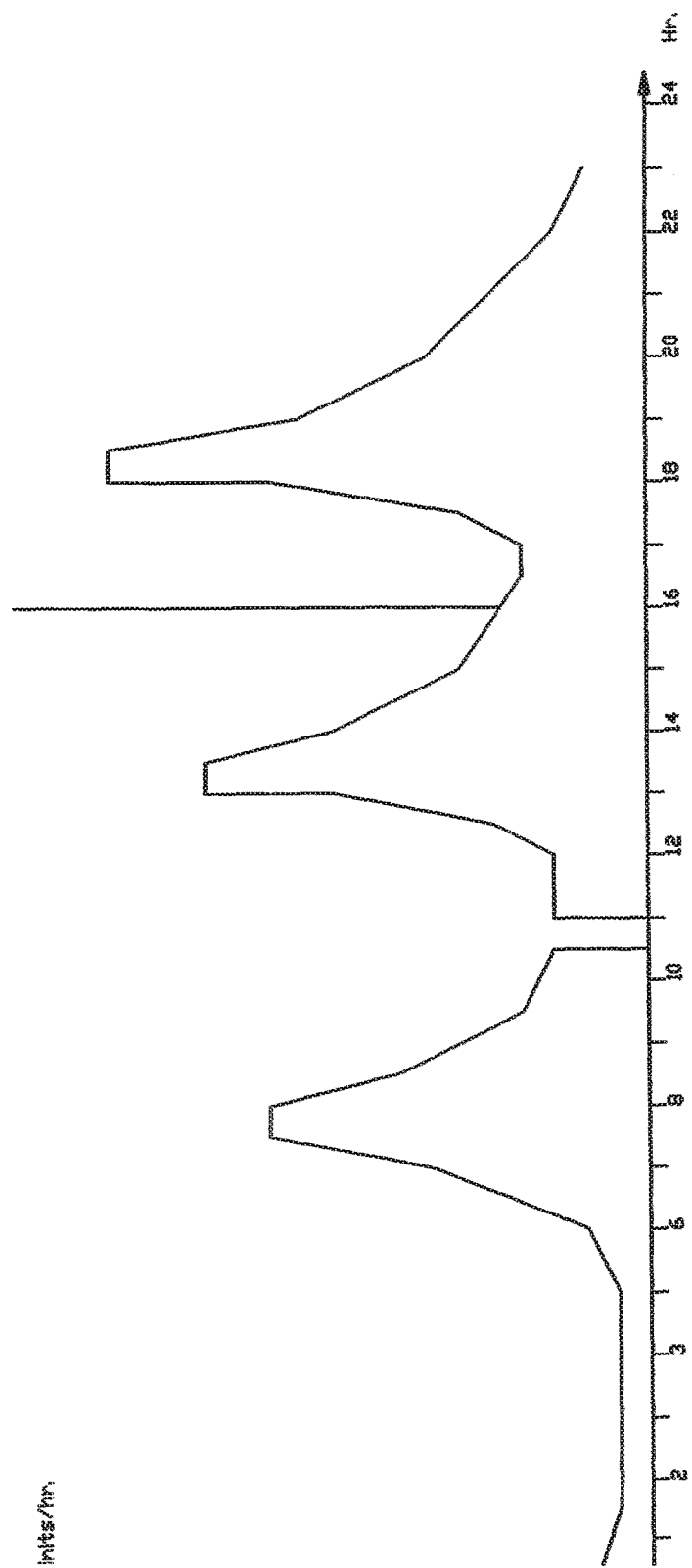

Referring now to FIG. 19, the graph illustrates a dispensing program which may be used for the pumps type 3-6 where the flow varies according to time and/or to input data.

The programming controller 29 may be a mobile wire-less communication device such as a cellular telephone communicating with the dispensing device by audio signals transmitted to and received from the transmitter/receiver 28. The transmissions should be preceded and terminated by an identification code to avoid disruption of the programming of the device by extraneous audio signals. Other signal identification or protection procedures such as encryption may be utilized. The audio signals may be converted to controlling signals for altering the programming of the re-programmable computing unit mounted in the circuit board 27.

Signal conversion means may be provided for converting the audio signals received by the receiver into input signals for the computing means and for converting output signals from the computing means into audio signals for being transmitted by the loudspeaker.

Wire-less so-called SMS signals may also be utilized for transferring information between a wire-less mobile communications unit and the dispensing device, for instance by means of IR signals or so-called Bluetooth communication technology.

Although the basic concept of the invention is that the entire device is disposable, a variation may be that the receiver/transmitter unit 28 with recording and play back components and corresponding battery and perhaps circuit board with computing means is reusable and may be releasably received in a holder provided on the disposable portion of the device.

The invention claimed is:

1. A medicine dispensing system, comprising:
   a wearable pump housing assembly, the wearable pump housing assembly configured to house a medicine reservoir in an interior space such that the medicine reservoir extends in a longitudinal direction along a length of the wearable pump housing assembly;
   a piston movably arranged in the housing assembly to dispense insulin from the medicine reservoir;
   a drive system to advance the piston toward the medicine reservoir;
   a bolus push button arranged on the wearable pump housing assembly so as to activate a bolus dispensing operation in which a bolus dosage of medicine is dispensed from the medicine reservoir;
   a combined microphone and audio speaker arranged on the wearable pump housing assembly for recording audio and emitting sounds upon manipulation of the bolus push button; and
   a control circuit in the pump housing assembly to communicate drive signals to the drive system to cause the dispensation of the insulin, the control circuit including: a programmable unit that stores a programmed dosage schedule.

2. The medicine dispensing system of claim 1, further comprising:
   a wireless communication receiver within the wearable pump housing assembly and in operative connection with the control circuit; and
   a wireless controller to communicate signals to the control circuit in the pump housing assembly indicative of the programmed dosage schedule, wherein the wireless controller is configured to receive user input of glucose level measurements.

3. The medicine dispensing system of claim 2, wherein the wireless controller includes a user interface display screen.

4. The medicine dispensing system of claim 1, further comprising:
   a recording and play back circuit operatively connected to the combined microphone and audio speaker such the recording and play back circuit is configured to, in conjunction with the combined microphone and audio speaker, record verbal messages and play back the verbal messages;
   wherein the recording and play back circuit is arranged inside the wearable pump housing assembly.

5. The medicine dispensing system of claim 4, wherein the recording and play back circuit is in operative connection with the control circuit.

6. The medicine dispensing system of claim 5, wherein the recording and play back circuit is part of the control circuit.

7. The medicine dispensing system of claim 5, wherein the control circuit is configured to control operation of the drive system in response to signals received from the recording and play back circuit.

8. The medicine dispensing system of claim 4, wherein the recording and play back circuit is configured to record audio signals received by the combined microphone and audio speaker in response to manipulation of the bolus push button.

9. The medicine dispensing system of claim 8, wherein the recording and play back circuit is configured to store a time value in association with the recorded audio signals.

10. The medicine dispensing system of claim 4, wherein the recording and play back circuit is configured to cause the combined microphone and audio speaker to play verbal messages in response to manipulation of the bolus push button.

11. The medicine dispensing system of claim 10, wherein the verbal messages played by the combined microphone and audio speaker are verbal messages that had been previously recorded by the recording and play back circuit using the combined microphone and audio speaker.

12. The medicine dispensing system of claim 4, wherein the recording and play back circuit is configured to cause the combined microphone and audio speaker to play a verbal message at a predetermined time.

13. The medicine dispensing system of claim 12, wherein the verbal message is received from a remote audio input device.

14. The medicine dispensing system of claim 13, wherein the remote audio input device is a mobile telephone.

15. The medicine dispensing system of claim 1, wherein the control circuit is configured to control operation of the drive system in response to audio signals received by the combined microphone and audio speaker.

16. The medicine dispensing system of claim 1, wherein the control circuit is configured to cause the combined microphone and audio speaker to play verbal messages.

17. The medicine dispensing system of claim 16, wherein the control circuit causes the combined microphone and audio speaker to play the verbal messages in response to manipulation of the bolus button.

18. The medicine dispensing system of claim 16, wherein the control circuit causes the combined microphone and audio speaker to play the verbal messages in response to the occurrence of predetermined times associated with the verbal messages.

19. The medicine dispensing system of claim 16, wherein the control circuit causes the combined microphone and audio speaker to play the verbal messages in response to identification of a particular activity of the medicine dispensing system.

20. The medicine dispensing system of claim 1, further comprising:
a wireless controller to communicate signals to the control circuit in the pump housing assembly indicative of the programmed dosage schedule, wherein the wireless controller is configured to communicate with the control circuit via audio signals transmitted to and received from the combined microphone and audio speaker.

* * * * *